United States Patent
Ziyatdinov et al.

(10) Patent No.: US 11,999,983 B2
(45) Date of Patent: Jun. 4, 2024

(54) **METHOD FOR PRODUCING BASIC L-amino ACIDS OR SALTS THEREOF BY FERMENTATION OF AN *Enterobacteriaceae* BACTERIUM**

(71) Applicant: AJINOMOTO CO., INC., Tokyo (JP)

(72) Inventors: Mikhail Kharisovich Ziyatdinov, Msocow (RU); Yulia Georgievna Rostova, Moscow (RU); Olga Nikolaevna Igonina, Moscow (RU); Andrei Viacheslavovich Kniazev, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 261 days.

(21) Appl. No.: 17/354,628

(22) Filed: Jun. 22, 2021

(65) Prior Publication Data

US 2021/0317487 A1    Oct. 14, 2021

Related U.S. Application Data

(63) Continuation of application No. PCT/JP2019/050844, filed on Dec. 25, 2019.

(30) Foreign Application Priority Data

Dec. 27, 2018   (RU) .............. RU2018147065

(51) Int. Cl.
| | | |
|---|---|---|
| C12P 13/10 | (2006.01) | |
| C07K 14/245 | (2006.01) | |
| C12N 1/20 | (2006.01) | |
| C12P 13/08 | (2006.01) | |
| C12P 13/24 | (2006.01) | |
| C12R 1/18 | (2006.01) | |
| C12R 1/19 | (2006.01) | |

(52) U.S. Cl.
CPC ............ *C12P 13/10* (2013.01); *C07K 14/245* (2013.01); *C12N 1/20* (2013.01); *C12P 13/08* (2013.01); *C12P 13/24* (2013.01); *C12R 2001/18* (2021.05); *C12R 2001/19* (2021.05)

(58) Field of Classification Search
None
See application file for complete search history.

(56) References Cited

U.S. PATENT DOCUMENTS

| | | |
|---|---|---|
| 4,278,765 A | 7/1981 | Debabov et al. |
| 4,346,170 A | 8/1982 | Sano et al. |
| 5,661,012 A | 8/1997 | Sano et al. |
| 5,827,698 A | 10/1998 | Kikuchi et al. |
| 5,965,391 A | 10/1999 | Reinscheid et al. |
| 6,040,160 A | 3/2000 | Kojima et al. |
| 6,258,554 B1 | 7/2001 | Ikeda et al. |
| 6,897,048 B2 | 5/2005 | Sakanyan et al. |
| 2006/0216796 A1 | 9/2006 | Hashiguchi et al. |
| 2009/0298135 A1 | 12/2009 | Maier et al. |
| 2017/0137853 A1 | 5/2017 | Bae et al. |

FOREIGN PATENT DOCUMENTS

| | | |
|---|---|---|
| CN | 105886449 A | 8/2016 |
| EP | 0685555 A1 | 12/1995 |
| EP | 1170361 A2 | 1/2002 |
| EP | 1445310 B2 | 6/2016 |
| EP | 2814945 B1 | 8/2017 |
| KR | 10-1825777 B1 | 2/2018 |
| RU | 2003677 C1 | 11/1993 |
| RU | 2119536 C1 | 9/1998 |
| WO | WO95/16042 A1 | 6/1995 |
| WO | WO96/15246 A1 | 5/1996 |
| WO | WO2011/152568 A1 | 12/2011 |
| WO | WO2015/030019 A1 | 3/2015 |
| WO | WO2015/064454 A1 | 5/2015 |

OTHER PUBLICATIONS

Liu et al. (AEM, vol. 81, No. 22, 2015, pp. 7753-7766).*
Vogel, H. J., et al., "Acetylornithinase (*Escherichia coli*)," Methods Enzymol. 1970;17A:265-269.
Eckhardt, T., et al., "Isolation and Characterization of Mutants with a Feedback Resistant N-Acetylglutamate Synthase in *Escherichia coli* K 12," Molec. Gen. Genet. 1975;138:225-232.
EcoCyc Database, https://ecocyc.org/, accession ID: G7833, downloaded Jun. 4, 2021, 3 pp.
Saier, Jr., M. H., et al., "The Transporter Classification Database (TCDB): recent advances," Nucleic Acids Res. 2016, vol. 44, Database issue, pp. D372-D379.
Jack, D. L., et al., "The amino acid/polyamine/organocation (APC) superfamily of transporters specific for amino acids, polyamines and organocations," Microbiol. 2000;146:1797-1814.
Saier Jr., M. H., et al., "The Transporter Classification Database," Nucleic Acids Res. 2014, vol. 42, Database issue, pp. D251-D258.
Liu, Q., et al., "YjeH Is a Novel Exporter of L-Methionine and Branched-Chain Amino Acids in *Escherichia coli*," Appl. Environmen. Microbiol. 2015;81(22):7753-7766.
Maier, T., et al., "Process of fermentative production of L-methionine; Sequence 1 from Patent EP1445310," Database accession No. CQ848866, Aug. 19, 2004, 1 pg.
Huang, J.-F., et al., "Metabolic Engineering of *Escherichia coli* for Microbial Production of L-Methionine," Biotechnol. Bioeng. 2017;114(4):843-851.
International Search Report for PCT Patent App. No. PCT/JP2019/050844 dated Apr. 17, 2020.
Written Opinion of the International Search Authority for PCT Patent App. No. PCT/JP2019/050844 dated Apr. 17, 2020.

* cited by examiner

*Primary Examiner* — Hope A Robinson
(74) *Attorney, Agent, or Firm* — Cermak & McGowan LLP; Shelly Guest Cermak

(57) ABSTRACT

The present invention provides a method for producing a basic L-amino acid, for example, L-ornithine L-citrulline, L-arginine, L-histidine, and L-lysine by fermentation using a bacterium belonging to the family Enterobacteriaceae which has been modified to overexpress a gene encoding a protein having L-methionine/branched chain amino acid exporter activity.

5 Claims, No Drawings

Specification includes a Sequence Listing.

METHOD FOR PRODUCING BASIC L-amino ACIDS OR SALTS THEREOF BY FERMENTATION OF AN *Enterobacteriaceae* BACTERIUM This application is a Continuation of, and claims priority under 35 U.S.C. § 120 to, International Application No. PCT/JP2019/050844, filed Dec. 25, 2019, and claims priority therethrough under 35 U.S.C. § 119 to Russian Patent Application No. 2018147065, filed Dec. 27, 2018, the entireties of which are incorporated by reference herein. Also, the Sequence Listing filed electronically herewith is hereby incorporated by reference (File name: 2021-06-22T_US-630_Seq_List; File size: 17 KB; Date recorded: Jun. 22, 2021).

FIELD OF THE INVENTION

The present invention relates generally to the microbiological industry, and specifically to a method for producing a basic L-amino acid by fermentation of a bacterium belonging to the family Enterobacteriaceae which has been modified to overexpress a gene encoding a protein having L-methionine/branched-chain amino acid exporter activity, so that production of the basic L-amino acid is enhanced as compared with an unmodified bacterium.

DESCRIPTION OF THE RELATED ART

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acids production yields have been reported, including transformation of microorganisms with recombinant DNA (see, for example, U.S. Pat. No. 4,278,765 A) and alteration of expression regulatory regions such as promoters, leader sequences, and/or attenuators, or others known to persons skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes which are involved in degradation of the target L-amino acid, genes which divert the precursors of the target L-amino acid from the L-amino acid biosynthetic pathway, genes involved in the redistribution of the carbon, nitrogen, sulfur, and phosphate fluxes, and genes encoding toxins, etc.

The biosynthetic pathways for L-ornithine, L-citrulline, and L-arginine in bacteria are related. In particular, in bacteria such as bacteria belonging to the family Enterobacteriaceae such as, for example, *Escherichia coli* (*E. coli*) a linear pathway for L-arginine biosynthesis takes place, and it includes eight steps until L-arginine is formed from L-glutamate via L-ornithine and L-citrulline formation (Vogel H. J. and MacLellan W. L., Acetylornithinase (*Escherichia coli*), *Methods Enzymol.*, 1970, 17A:265-269). The biosynthesis is initiated by acetylating L-glutamate with amino acid N-acetyltransferase (EC 2.3.1.1, also referred to as N-acetyl-L-glutamate synthetase) encoded by the argA gene. The follow-up biosynthetic reactions are catalyzed by the enzymes commonly referred to as N-acetylglutamate kinase, N-acetyl-γ-glutamylphosphate reductase, N-acetylornithine aminotransferase, N-acetylornithine deacetylase, ornithine carbamoyltransferase, argininosuccinate synthase, and argininosuccinate lyase encoded by the argB, argC, argD, argE, argF or argI, argG, and argH genes, respectively.

An *E. coli* bacterium having the native linear pathway has been modified to contain the argJ gene from *Bacillus stearothermophilus* or *Thermotoga neapolitana*, which encodes bifunctional ArgJ enzyme, to initiate the less energy consuming cyclic pathway and thus to increase production of L-arginine by the modified bacterium (U.S. Pat. No. 6,897,048 B2).

In microorganisms utilizing the native linear biosynthetic pathway or having a modified linear pathway that functions as the cyclic pathway, the amino acid N-acetyltransferase (N-acetyl-L-glutamate synthetase) (ArgA) may be required to initiate and support L-arginine biosynthesis through the N-acetylglutamate supply. Therefore, to increase production of L-arginine by a recombinant *E. coli* strain, the number of copies of the argA gene can be increased by cloning the wild-type argA gene on plasmid vectors and incorporating them into the strain having the argJ gene cloned (U.S. Pat. No. 6,897,048 B2). Alternatively, the argA gene encoding a mutant amino acid N-acetyltransferase resistant to feedback inhibition by L-arginine (Eckhardt T. et al., *Mol. Gen. Genet.*, 1975, 138:225-232) can be introduced into *E. coli* strain to improve L-arginine production (EP1170361 A2).

Methods for producing L-ornithine (also known as (+)-(S)-2,5-diaminovaleric acid) by culturing a recombinant L-ornithine-producing bacterium in a medium are known (WO2015064454 and WO2015030019). In these methods, an L-ornithine-producing bacterium was obtained from an L-arginine-producing bacterium by inactivation of ornithine carbamoyltransferase encoded by argF and argI genes.

Methods for producing L-citrulline (also known as 2-amino-5-(carbamoylamino)pentanoic acid) by culturing in a medium a recombinant L-citrulline-producing bacterium are known (WO2015064454 and WO2015030019). In these methods, L-citrulline-producing bacterium was obtained from an L-arginine-producing bacterium by inactivation of argininosuccinate synthase encoded by argG gene.

Methods for production of L-histidine and L-lysine by fermentation of bacteria are also known (see, for example, Russian patent Nos. 2003677 C1 and 2119536 C1, U.S. Pat. No. 6,258,554 B1; and U.S. Pat. Nos. 4,346,170 A and 5,827,698 A, accordingly).

A YjeH protein native to *E. coli*, which is encoded by a yjeH gene, is characterized as an L-methionine/branched-chain amino acid exporter (EcoCyc database, ecocyc.org/, accession ID: G7833). In the Transporter Classification Database, YjeH is classified as a hydrophobic amino acid efflux transporter that exports L-methionine and other neutral and hydrophobic amino acids such as L-leucine, L-isoleucine, and L-valine (Saier M. H. Jr. et al., The Transporter Classification Database (TCDB): recent advances, *Nucleic Acids Res.*, 2016, 44(D1):D372-9; doi: 10.1093/nar/gkv1103). The YjeH protein is a member of the Amino Acid Efflux (AAE) Family within the Amino Acid-Polyamine-Organocation (APC) Superfamily of transporters; transporter classification number (TCID) 2.A.3.13.1 (Jack D. L. et al., The amino acid/polyamine/organocation (APC) superfamily of transporters specific for amino acids, polyamines and organocations, *Microbiology*, 2000, 146 (8):1797-1814; Saier M. H. et al., The transporter classification database, *Nucleic. Acids Res.*, 2014, 42(1):D251-8). YjeH is predicted to contain 12 transmembrane a helices, 10 of which form an inverted repeat fold that is characteristic of the APC superfamily (Liu Q. et al., 2015)

Methods for producing amino acids that have hydrophobic or uncharged (that is, neutral) side chains, or derivatives of these amino acids, by fermentation of a bacterium that has been modified to, at least, overexpress the yjeH gene are known. For example, a method for producing L-methionine by fermentation of a microorganism having increased activity of the yjeH gene product or its functional allele variant is known (EP1445310 B2). In another method, L-methionine was produced using a recombinant *E. coli* bacterium into which, at least, the yjeH gene has been transferred (CN105886449 A). A method for producing O-acetylhomoserine and L-methionine using an *Escherichia* microorganism having enhanced activity of YjeH protein has also been reported (KR101825777B1). Also, a method of preparing methionine or tryptophan by culturing an *E. coli* cell that has been modified to reduce ppGppase activity and overexpress, at least, a nucleic acid sequence that encodes YjeH enzyme is known (EP2814945 B1).

However, technical problems still exist in methods for improving production of a basic L-amino acid by fermentation of a bacterium belonging to the family Enterobacteriaceae that has been modified to overexpress a gene encoding a protein having L-methionine/branched-chain amino acid exporter activity. In particular, no data has been previously reported that describes the effect of overexpression of the yjeH gene on production of a basic L-amino acid by fermentation of a bacterium belonging to the family Enterobacteriaceae.

SUMMARY OF THE INVENTION

An improved method of producing a basic L-amino acid by fermentation of a bacterium belonging to the family Enterobacteriaceae is described herein. According to the presently disclosed subject matter, production of a basic L-amino acid by fermentation of a bacterium belonging to the family Enterobacteriaceae can be increased. Specifically, production of a basic L-amino acid as described herein by fermentation of a bacterium belonging to the family Enterobacteriaceae can be improved when the bacterium is modified to overexpress a gene encoding a protein having L-methionine/branched-chain amino acid exporter activity, so that the production of the basic L-amino acid by the modified bacterium can be enhanced.

The present invention thus provides the following.

It is an aspect of the invention to provide a method for producing a basic L-amino acid comprising:

(i) cultivating a basic L-amino acid-producing bacterium belonging to the family Enterobacteriaceae in a culture medium to produce and accumulate the basic L-amino acid in the culture medium or cells of the bacterium, or both, and (ii) collecting the basic L-amino acid from the culture medium or the cells, or both, wherein said bacterium has been modified to overexpress a gene encoding a protein having L-methionine/branched-chain amino acid exporter activity.

It is another aspect of the invention to provide the method as described above, wherein said basic L-amino acid is selected from the group consisting of L-ornithine, L-citrulline, L-arginine, L-histidine, L-lysine, and combinations thereof.

It is another aspect of the invention to provide the method as described above, wherein said protein having L-methionine/branched-chain amino acid exporter activity is selected from the group consisting of:

(A) a YjeH protein, (B) a protein comprising the amino acid sequence shown in SEQ ID NO: 2, (C) a protein comprising the amino acid sequence shown in SEQ ID NO: 2, but which includes substitution, deletion, insertion, and/or addition of about 1 to 100 amino acid residues, and wherein said protein has L-methionine/branched-chain amino acid exporter activity, and (D) a protein comprising an amino acid sequence having an identity of amino acid residues of not less than 70% with respect to the entire amino acid sequence shown in SEQ ID NO: 2, and wherein said protein has L-methionine/branched-chain amino acid exporter activity.

It is another aspect of the invention to provide the method as described above, wherein said protein having L-methionine/branched-chain amino acid exporter activity is encoded by a DNA selected from the group consisting of:

(a) a yjeH gene, (b) a DNA comprising the nucleotide sequence shown in SEQ ID NO: 1, (c) a DNA encoding a protein comprising the amino acid sequence shown in SEQ ID NO: 2, but which includes substitution, deletion, insertion and/or addition of 1 to 100 amino acid residues, and wherein said protein has L-methionine/branched-chain amino acid exporter activity, (d) a DNA encoding a protein comprising an amino acid sequence having an identity of amino acid residues of not less than 70% with respect to the entire amino acid sequence shown in SEQ ID NO: 2, and wherein said protein has L-methionine/branched-chain amino acid exporter activity, and (e) a DNA which is a variant nucleotide sequence of SEQ ID NO: 1 due to the degeneracy of the genetic code.

It is another aspect of the invention to provide the method as described above, wherein the gene encoding a protein having L-methionine/branched-chain amino acid exporter activity is overexpressed by introducing that gene, increasing the copy number of that gene and/or by modifying an expression regulatory region of that gene, so that the expression of said gene is enhanced as compared with a non-modified bacterium.

It is another aspect of the invention to provide the method as described above, wherein said bacterium belongs to the genus *Escherichia* or *Pantoea*.

It is another aspect of the invention to provide the method as described above, wherein said bacterium is *Escherichia coli* or *Pantoea ananatis*.

Still other objects, features, and attendant advantages of the present invention will become apparent to those skilled in the art from a reading of the following detailed description of embodiments constructed in accordance therewith.

DETAILED DESCRIPTION OF THE INVENTION

1. Bacterium

The bacterium as described herein is an L-amino acid-producing bacterium belonging to the family Enterobacteriaceae that has been modified to overexpress a gene encoding a protein having L-methionine/branched-chain amino acid exporter activity. The bacterium as described herein can be used in the method as described herein. Hence, the explanations given hereinafter to the bacterium can be similarly applied to any bacterium that can be used interchangeably or equivalently in the method as described herein.

The bacterium that can be used in the method as described herein can be a bacterium that is appropriately selected depending on the kind of the target L-amino acid which is produced using the method. Therefore, the bacterium can be a basic L-amino acid-producing bacterium. Specifically, the bacterium can be an L-ornithine-producing bacterium when the target L-amino acid is L-ornithine. The derivative L-amino acids L-citrulline and L-arginine can be obtained biosynthetically from L-ornithine, and therefore, the bacterium can also be an L-citrulline-producing bacterium when the target L-amino acid is L-citrulline, or an L-arginine-producing bacterium when the target L-amino acid is L-arginine. The bacterium as described herein also can be an L-histidine or an L-lysine-producing bacterium when, accordingly, the target L-amino acid is L-histidine or L-lysine. Examples of basic L-amino acid-producing bacteria are described herein.

Any basic L-amino acid-producing bacterium belonging to the family Enterobacteriaceae can be used in the method as described herein, provided that the bacterium can be modified to overexpress a gene encoding a protein having L-methionine/branched-chain amino acid exporter activity. For example, a basic L-amino acid-producing bacterium belonging to the family Enterobacteriaceae can be used in the method as described herein, provided that the bacterium can be modified to overexpress a gene encoding a protein having L-methionine/branched-chain amino acid exporter activity, so that the production of a basic L-amino acid by the bacterium can be enhanced as compared with a non-modified bacterium.

The phrase "a basic L-amino acid-producing bacterium" may be used interchangeably or equivalently to the phrase "a bacterium that is able to produce a basic L-amino acid" or the phrase "a bacterium having an ability to produce a basic L-amino acid".

The phrase "a basic L-amino acid-producing bacterium" can mean a bacterium belonging to the family Enterobacteriaceae which has an ability to produce, excrete or secrete, and/or cause accumulation of a basic L-amino acid in a culture medium and/or cells of the bacterium when the bacterium is cultured in the medium.

The phrase "a basic L-amino acid-producing bacterium" can also mean a bacterium which has an ability to produce, excrete or secrete, and/or cause accumulation of a basic L-amino acid in a culture medium in an amount larger than a non-modified bacterium. The phrase "a non-modified bacterium" may be used interchangeably or equivalently to the phrase "a non-modified strain". The phrase "a non-modified strain" can mean a control strain that has not been modified to overexpress a gene encoding a protein having L-methionine/branched-chain amino acid exporter activity. Examples of the non-modified strain can include a wild-type or parental strain such as, for example, *Escherichia coli* (*E. coli*) K-12 strains such as W3110 (ATCC 27325) and MG1655 (ATCC 47076), and *Pantoea ananatis* (*P. ananatis*) AJ13355. The phrase "a basic L-amino acid-producing bacterium" can also mean a bacterium that is able to cause accumulation in the medium of an amount, for example, not less than 0.1 g/L, not less than 0.5 g/L, or not less than 1.0 g/L of a basic L-amino acid. The phrase "a basic L-amino acid-producing bacterium" can also mean a bacterium which has an ability to produce, excrete or secrete, and/or cause accumulation of a basic L-amino acid in a culture medium in an amount larger than a non-modified bacterium, and is able to cause accumulation in the medium of an amount, for example, not less than 0.1 g/L, not less than 0.5 g/L, or not less than 1.0 g/L of the basic L-amino acid.

The bacterium may inherently have the ability to produce a basic L-amino acid or may be modified to have an ability to produce a basic L-amino acid. Such modification can be attained by using, for example, a mutation method or DNA recombination techniques. The bacterium can be obtained by overexpressing a gene encoding a protein having L-methionine/branched-chain amino acid exporter activity in a bacterium that inherently has the ability to produce a basic L-amino acid, or in a bacterium that has been already imparted with the ability to produce a basic L-amino acid. Alternatively, the bacterium can be obtained by imparting the ability to produce a basic L-amino acid to a bacterium already modified to overexpress a gene encoding a protein having L-methionine/branched-chain amino acid exporter activity. Alternatively, the bacterium may have been imparted with the ability to produce a basic L-amino acid by being modified to overexpress a gene encoding a protein having L-methionine/branched-chain amino acid exporter activity. The bacterium as described herein can be obtained, specifically, for example, by modifying a bacterial strain described hereinafter.

The phrase "an ability to produce a basic L-amino acid" can mean the ability of a bacterium to produce, excrete or secrete, and/or cause accumulation of a basic L-amino acid in a culture medium and/or cells of the bacterium when the bacterium is cultured in the medium. The phrase "an ability to produce a basic L-amino acid" can specifically mean the ability of a bacterium belonging to the family Enterobacteriaceae to produce, excrete or secrete, and/or cause accumulation of a basic L-amino acid in a culture medium and/or cells of the bacterium to such a level that the basic L-amino acid can be collected from the culture medium and/or the cells when the bacterium is cultured in the medium.

The phrase "cultured" with reference to a bacterium which can be used in the method as described herein may be used interchangeably or equivalently to the phrase "cultivated", or the like, that are well-known to persons skilled in the art.

The bacterium can produce a basic L-amino acid either alone or as a mixture of the basic L-amino acid and one or more kinds of substances that are different from the basic L-amino acid. For example, the bacterium can produce a basic L-amino acid either alone or as a mixture of the basic L-amino acid and one or more kinds of amino acids that are different from the basic L-amino acid such as, for example, L-amino acids that are not basic L-amino acids. Moreover, for example, the bacterium can produce a target basic L-amino acid either alone or as a mixture of the target basic L-amino acid and one or more other basic L-amino acids that are different from the target basic L-amino acid. In other words, it is acceptable that the bacterium can produce two or more basic L-amino acids as a mixture. Furthermore, for example, the bacterium can produce a basic L-amino acid either alone or as a mixture of the basic L-amino acid and one or more kinds of other organic acids such as, for example, carboxylic acids.

Examples of L-amino acids include, but are not limited to, L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

The phrase "a basic L-amino acid" can mean an L-amino acid that has the radical side chain which is positively charged at neutral pH (pH 7). Examples of basic L-amino acids include, but are not limited to, L-arginine, L-citrulline, L-histidine, L-lysine, and L-ornithine.

Examples of carboxylic acids include, but are not limited to, formic acid, acetic acid, citric acid, butyric acid, lactic acid, and propionic acid, and derivatives thereof.

The phrases "L-amino acid" and "carboxylic acid" can refer not only to an L-amino acid and a carboxylic acid in a free form, but can also refer to a derivative form thereof, such as a salt, a hydrate, an adduct, or a combination of these. An adduct can be a compound formed by the L-amino acid or the carboxylic acid in combination with another organic or inorganic compound. Hence, the phrases "L-amino acid" and "carboxylic acid" can mean, for example, an L-amino acid and a carboxylic acid in a free form, a derivative form, or a mixture of these. The phrases "L-amino acid" and "carboxylic acid" can particularly mean, for example, an L-amino acid and a carboxylic acid in a free form, a salt thereof, or a mixture of these. The phrases "L-amino acid" and "carboxylic acid" can refer to, for example, any of sodium, potassium, ammonium, mono-, di- and trihydrate, mono- and dichlorhydrate, and so forth salts of them. Unless otherwise stated, the phrases "L-amino acid" and "carboxylic acid" without referring to hydration state, such as the phrases "an L-amino acid or a carboxylic acid in a free form" and "a salt of an L-amino acid or a carboxylic acid", can refer to an L-amino acid and a carboxylic acid not in a hydrate form, or can refer to a hydrate of an L-amino acid and a carboxylic acid.

Examples of the bacteria belonging to the family Enterobacteriaceae can include bacteria belonging to the genera *Enterobacter, Erwinia, Escherichia, Klebsiella, Morganella, Pantoea, Photorhabdus, Providencia, Salmonella, Yersinia,* and so forth. Such bacteria can have the ability to produce a basic L-amino acid. Specifically, bacteria classified into the family Enterobacteriaceae according to the taxonomy used in the NCBI (National Center for Biotechnology Information) database (www.ncbi.nlm.nih.gov/Taxonomy/Browser/wwwtax.cgi?id=543) can be used. Particular examples of the bacteria belonging to the family Enterobacteriaceae include bacteria belonging to the genera *Escherichia, Enterobacter,* and *Pantoea.*

*Escherichia* bacteria are not particularly limited, and examples thereof include those described in the work of Neidhardt et al. (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, $2^{nd}$ ed. ASM Press, Washington, D.C., 1996). The species *Escherichia coli* (*E. coli*) is a particular example of *Escherichia* bacteria. Specific examples of *E. coli* include *E. coli* K-12 strain, which is a prototype wild-type strain, such as *E. coli* W3110 (ATCC 27325), *E. coli* MG1655 (ATCC 47076), and so forth.

Examples of the *Enterobacter* bacteria include *Enterobacter agglomerans, Enterobacter aerogenes,* and so forth. Examples of the *Pantoea* bacteria include *Pantoea ananatis* (*P. ananatis*), and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to either genus *Enterobacter* or *Pantoea* may be used so long as it is a bacterium classified into the family Enterobacteriaceae. Specific examples of *P. ananatis* include *Pantoea ananatis* AJ13355 strain (FERM BP-6614), AJ13356 strain (FERM BP-6615), AJ13601 strain (FERM BP-7207) and derivatives thereof. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

These strains are available from, for example, the American Type Culture Collection (ATCC; Address: P.O. Box 1549, Manassas, VA 20108, United States of America). That is, registration numbers are assigned to the respective strains, and the strains can be ordered by using these registration numbers (refer to lgcstandards-atcc.org). The registration numbers of the strains are listed in the catalogue of the American Type Culture Collection. These strains can also be obtained from, for example, the depositories at which the respective strains were deposited.

To impart or enhance a basic L-amino acid-producing ability, methods conventionally employed in the breeding of amino acid-producing strains of coryneform bacteria, *Escherichia* bacteria, and so forth (refer to "Amino Acid Fermentation", Gakkai Shuppan Center (Ltd.), 1st Edition, published May 30, 1986, pp. 77-100) can be used. Examples of such methods include, for example, acquiring an auxotrophic mutant strain, acquiring a basic L-amino acid analogue-resistant strain, acquiring a metabolic regulation mutant strain, and constructing a recombinant strain in which the activity of a basic L-amino acid biosynthetic enzyme is enhanced. In the breeding of basic L-amino acid-producing bacteria, one of the above-described properties such as auxotrophy, analogue resistance, and metabolic regulation mutation may be imparted alone, or two or three or more of such properties may be imparted in combination. Also, in the breeding of basic L-amino acid-producing bacteria, the activity of one of basic L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having a basic L-amino acid-producing ability can be obtained by subjecting a parental strain or wild-type strain to a usual mutagenesis treatment, and then selecting a strain exhibiting autotrophy, analogue resistance, or a metabolic regulation mutation, and having a basic L-amino acid-producing ability from the obtained mutant strains. Examples of the usual mutagenesis treatment include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

A basic L-amino acid-producing ability can also be imparted or enhanced by enhancing the activity of an enzyme involved in biosynthesis of an objective basic L-amino acid. An enzyme activity can be enhanced by, for example, modifying a bacterium so that the expression of a gene encoding the enzyme is enhanced. Methods for enhancing gene expression are described in WO00/18935, EP1010755A, and so forth. Methods for overexpressing a gene encoding a protein having L-methionine/branched-chain amino acid exporter activity described below can be similarly applied similarly to enhancing the activity of an enzyme or enhancing the expression of a gene encoding the enzyme.

Furthermore, a basic L-amino acid-producing ability can also be imparted or enhanced by reducing the activity of an enzyme that catalyzes a reaction branching away from the biosynthetic pathway of an objective basic L-amino acid to generate a compound other than the objective basic L-amino acid. The phrase "enzyme that catalyzes a reaction branching away from the biosynthetic pathway of an objective basic L-amino acid to generate a compound other than the objective basic L-amino acid" referred to herein can also refer to an enzyme involved in decomposition of the objective basic L-amino acid.

Hereinafter, basic L-amino acid-producing bacteria and methods for imparting or enhancing a basic L-amino acid-producing ability will be specifically exemplified. All of the properties of the basic L-amino acid-producing bacteria and modifications for imparting or enhancing a basic L-amino acid-producing ability may be used independently or in any appropriate combination.

<L-Arginine-producing Bacteria>

Examples of L-arginine-producing bacteria and parental strains which can be used to derive L-arginine-producing bacteria include, for example, strains in which the activity or activities of one or more of the L-arginine biosynthetic enzymes are enhanced. Examples of such enzymes include, but are not limited to, N-acetylglutamate synthase (argA), N-acetylglutamate kinase (argB), N-acetyl-γ-glutamylphosphate reductase (argC), N-acetylornithine aminotransferase (argD), acetylornithine deacetylase (argE), ornithine carbamoyltransferase (argF, argI), argininosuccinate synthase (argG), argininosuccinate lyase (argH), ornithine acetyltransferase (argJ), and carbamoyl phosphate synthetase (carAB). Shown in the parentheses after the names of the enzymes are examples of genes encoding the enzymes (the same nomenclature shall similarly apply when reciting proteins/enzymes and genes hereinafter). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild type enzyme (EP1170361A) can preferably be used.

Specific examples of L-arginine-producing bacteria and parental strains which can be used to derive L-arginine-producing bacteria include, for example, strains belonging to the genus *Escherichia* such as the *E. coli* 237 strain (VKPM B-7925, US2002-058315A1), derivative strains thereof into which the argA gene encoding a mutant N-acetyl glutamate synthase has been introduced (Russian Patent Application No. 2001112869, EP1170361A1), *E. coli* 382 strain derived from the 237 strain and having an improved acetic acid-assimilating ability (VKPM B-7926, EP1170358A1), and *E. coli* 382ilvA+ strain, which is a strain obtained from the 382 strain by introducing the wild-type ilvA gene from *E. coli* K-12 strain thereto. The *E. coli* strain 237 was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7925, and the deposit was converted to an international deposit under the provisions of Budapest Treaty on May 18, 2001. The *E. coli* 382 strain was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7926, and the deposit was converted to an international deposit under the provisions of Budapest Treaty on May 18, 2001.

Examples of L-arginine-producing bacteria and parental strains which can be used to derive L-arginine-producing bacteria also include strains having resistance to amino acid analogues, and so forth. Examples of such strains include *E. coli* mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (Japanese Patent Laid-open (Kokai) No. 56-106598).

<L-Citrulline-Producing Bacteria and L-Ornithine-Producing Bacteria>

L-citrulline and L-ornithine are intermediates in the biosynthetic pathway of L-arginine. Hence, examples of L-citrulline- or L-ornithine-producing bacteria and parental strains which can be used to derive L-citrulline- or L-ornithine-producing bacteria include, for example, strains in which the activity or activities of one or more of the L-arginine biosynthetic enzymes are enhanced. Examples of such enzymes include, but are not limited to, N-acetylglutamate synthase (argA), N-acetylglutamate kinase (argB), N-acetyl-γ-glutamylphosphate reductase (argC), N-acetylornithine aminotransferase (argD), acetylornithine deacetylase (argE), ornithine carbamoyltransferase (argF, argI), ornithine acetyltransferase (argJ), and carbamoyl phosphate synthetase (carAB), for L-citrulline. Furthermore, examples of such enzymes include, but are not limited to, N-acetylglutamate synthase (argA), N-acetylglutamate kinase (argB), N-acetyl-γ-glutamylphosphate reductase (argC), N-acetylornithine aminotransferase (argD), acetylornithine deacetylase (argE), and ornithine acetyltransferase (argJ), for L-ornithine.

Specific examples of L-citrulline-producing bacteria and parental strains which can be used to derive L-citrulline-producing bacteria include, but are not limited to strains belonging to the genus *Escherichia* such as *E. coli* trains 237/pMADS11, 237/pMADS12, and 237/pMADS13, which have a mutant N-acetylglutamate synthase (Russian Patent No. 2215783, European Patent No. 1170361 B1, and U.S. Pat. No. 6,790,647 B2), *E. coli* strains 333 (VKPM B-8084) and 374 (VKPM B-8086), which have carbamoyl phosphate synthetase resistant to feedback inhibition (Russian patent No. 2,264,459), and *E. coli* strains having an increased activity of α-ketoglutarate synthase and having a modified activity of ferredoxin NADP reductase, pyruvate synthase, and/or α-ketoglutarate dehydrogenase (EP2133417A).

An L-citrulline-producing bacterium can be easily obtained from any L-arginine-producing bacterium such as, for example, *E. coli* 382 stain (VKPM B-7926), by inactivation of argininosuccinate synthase encoded by argG gene. Methods for inactivation of genes are described herein.

An L-ornithine-producing bacterium can be easily obtained from any L-arginine-producing bacterium such as, for example, *E. coli* 382 stain (VKPM B-7926), by inactivation of ornithine carbamoyltransferase encoded by argF and argI genes.

<L-Histidine-Producing Bacteria>

Examples of L-histidine-producing bacteria and parental strains which can be used to derive L-histidine-producing bacteria also include strains in which the activity or activities of one or more of the L-histidine biosynthetic enzymes are enhanced. Examples of such enzymes include, but are not limited to, ATP phosphoribosyltransferase (hisG), phosphoribosyl-ATP pyrophosphatase (hisE), phosphoribosyl-AMP cyclohydrolase (hisI), bifunctional phosphoribosyl-AMP cyclohydrolase/phosphoribosyl-ATP pyrophosphatase (hisIE), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

It is known that the L-histidine biosynthetic enzymes encoded by hisG and hisBHAFI are inhibited by L-histidine. Therefore, an L-histidine-producing ability can also be efficiently enhanced by, for example, introducing a mutation conferring resistance to the feedback inhibition into ATP phosphoribosyltransferase (Russian Patent Nos. 2,003,677 C1 and 2,119,536 C1).

Specific examples of L-histidine-producing bacteria and parental strains which can be used to derive L-histidine-producing bacteria also include, for example, strains belonging to the genus *Escherichia* such as *E. coli* strain 24 (VKPM B-5945, RU2003677 C1), *E. coli* NRRL B-12116 to B-12121 (U.S. Pat. No. 4,388,405), *E. coli* H-9342 (FERM BP-6675) and H-9343 (FERM BP-6676) (U.S. Pat. No. 6,344,347 B1), *E. coli* H-9341 (FERM BP-6674) (EP1085087 A2), and *E. coli* AI80/pFM201 (U.S. Pat. No. 6,258,554 B1), *E. coli* FERM-P 5038 and 5048, which have been transformed with a vector carrying a DNA encoding an L-histidine-biosynthetic enzyme (JP 56-005099 A), *E. coli* strains transformed with rht, a gene for an amino acid-export (EP1016710 A2), *E. coli* 80 strain, which has been imparted with sulfaguanidine, DL-1,2,4-triazole-3-alanine, and streptomycin-resistance (VKPM B-7270, RU2119536 C1), and *E. coli* MG1655+hisGr hisL'_Δ ΔpurR (RU2119536 and Doroshenko V. G. et al., The directed modification of *Escherichia coli* MG1655 to obtain histidine-producing mutants, *Prikl. Biochim. Mikrobiol.* (*Russian*), 2013, 49(2): 149-154).

<L-Lysine-Producing Bacteria>

Examples of L-lysine-producing bacteria and parental strains which can be used to derive L-lysine-producing bacteria include mutant strains belonging to the genus *Escherichia* and having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting bacteria belonging to the genus *Escherichia* to a conventional artificial mutagenesis treatment.

Examples of L-lysine-producing bacteria and parental strains which can be used to derive L-lysine-producing bacteria also include strains in which the activity or activities of one or more of the L-lysine biosynthetic enzymes is/are enhanced. Examples of such enzymes include, but are not limited to, genes encoding dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP1253195 A1). It is preferable to enhance the activity or activities of one or more of, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase, among these enzymes. In addition, L-histidine-producing bacteria and parental strains which can be used to derive L-histidine-producing bacteria may have an increased level of expression of the gene involved in energy efficiency (cyo) (EP1170376 A1), the gene encoding nicotinamide nucleotide transhydrogenase (pntAB) (U.S. Pat. No. 5,830,716 A), the ybjE gene (WO2005/073390), or combinations thereof. Since aspartokinase III (lysC) is subjected to feedback inhibition by L-lysine, a mutant lysC gene coding for an aspartokinase III desensitized to feedback inhibition by L-lysine (U.S. Pat. No. 5,932,453) may be used for enhancing the activity of this enzyme. Examples of the aspartokinase III desensitized to feedback inhibition by L-lysine include aspartokinase III derived from *Escherichia coli* and having one or more mutations, such as a mutation for replacing the methionine residue at position 318 with an isoleucine residue; a mutation for replacing the glycine residue at position 323 with an aspartic acid residue; and a mutation for replacing the threonine residue at position 352 with an isoleucine residue (U.S. Pat. Nos. 5,661,012 and 6,040,160). Furthermore, since dihydrodipicolinate synthase (dapA) is subjected to feedback inhibition by L-lysine, a mutant dapA gene coding for a dihydrodipicolinate synthase desensitized to feedback inhibition by L-lysine may be used for enhancing the activity of this enzyme. Examples of the dihydrodipicolinate synthase desensitized to feedback inhibition by L-lysine include dihydrodipicolinate synthase derived from *Escherichia coli* and having a mutation for replacing the histidine residue at position 118 with a tyrosine residue (U.S. Pat. No. 6,040,160).

L-lysine-producing bacteria or parental strains which can be used to derive L-lysine-producing bacteria may have a reduced or no activity of an enzyme that catalyzes a reaction which causes a branching off from the L-amino acid biosynthesis pathway and results in the production of another compound. Also, L-lysine-producing bacteria or parental strains which can be used to derive L-lysine-producing bacteria may have a reduced or no activity of an enzyme that negatively acts on L-lysine synthesis or accumulation. Examples of such enzymes include, but are not limited to, homoserine dehydrogenase, lysine decarboxylase (cadA, ldcC), and malic enzyme, and strains in which the activities of these enzymes are decreased or deleted are disclosed in WO95/23864, WO96/17930, WO2005/010175, and so forth. The lysine decarboxylase activity can be decreased or deleted by, for example, decreasing expression of both the cadA and ldcC genes encoding lysine decarboxylase. Expression of the both genes can be decreased by, for example, the method described in WO2006/078039.

Specific examples of bacterial strains useful for producing L-lysine include *E. coli* AJ11442 (FERM BP-1543, NRRL B-12185; see U.S. Pat. No. 4,346,170) and *E. coli* VL611. In these strains, feedback inhibition of aspartokinase by L-lysine is desensitized.

Specific examples of L-lysine-producing bacteria and parental strains which can be used to derive L-lysine-producing bacteria also include the *E. coli* WC196 strain (FERM BP-5252, U.S. Pat. No. 5,827,698), the *E. coli* WC196ΔcadAΔldcC strain (FERM BP-11027), also referred to as WC196LC, and the *E. coli* WC196ΔcadAΔldcC/pCABD2 strain (WO2006/078039).

The WC196 strain was bred from the W3110 strain, which was derived from *E. coli* K-12, by conferring AEC resistance to the W3110 strain (U.S. Pat. No. 5,827,698). The WC196 strain was designated *E. coli* AJ13069, deposited at the National Institute of Bioscience and Human Technology, Agency of Industrial Science and Technology, Ministry of International Trade and Industry (currently, independent administrative agency, National Institute of Technology and Evaluation, International Patent Organism Depositary (NITE IPOD), #120, 2-5-8 Kazusakamatari, Kisarazu-shi, Chiba, 292-0818, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

The WC196ΔcadAΔldcC strain was constructed from the WC196 strain by disrupting the cadA and ldcC genes which encode lysine decarboxylase. The WC196ΔcadAΔldcC strain was designated AJ110692 and deposited at the independent administrative agency, National Institute of Advanced Industrial Science and Technology, International Patent Organism Depositary (currently, independent administrative agency, National Institute of Technology and Evaluation, International Patent Organism Depositary (NITE IPOD), #120, 2-5-8 Kazusakamatari, Kisarazu-shi, Chiba-ken, 292-0818, Japan) on Oct. 7, 2008 as an international deposit under the accession number FERM BP-11027.

The WC196ΔcadAΔldcC/pCABD2 strain was constructed by introducing the plasmid pCABD2 containing lysine biosynthesis genes (U.S. Pat. No. 6,040,160) into the WC196ΔcadAΔldcC strain. The plasmid pCABD2 contains a mutant dapA gene derived from *Escherichia coli* and coding for a dihydrodipicolinate synthase (DDPS) having a mutation for desensitization to feedback inhibition by L-lysine (H118Y), a mutant lysC gene derived from *Escherichia coli* and coding for aspartokinase III having a mutation for desensitization to feedback inhibition by L-lysine (T352I), the dapB gene derived from *Escherichia coli* and coding for dihydrodipicolinate reductase, and the ddh gene derived from *Brevibacterium lactofermentum* and coding for diaminopimelate dehydrogenase.

Examples of L-lysine-producing bacteria and parental strains which can be used to derive L-lysine-producing bacteria also include *E. coli* AJIK01 (NITE BP-01520). The AJIK01 strain was designated *E. coli* AJ111046, and deposited at the independent administrative agency, National Institute of Technology and Evaluation, Patent Microorganisms Depositary (NITE NPMD, #122, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

The genes and proteins used for breeding basic L-amino acid-producing bacteria may have, for example, known nucleotide sequences and amino acid sequences of the genes and proteins exemplified above, respectively. Also, the genes and proteins used for breeding basic L-amino acid-producing bacteria may be variants of the genes and proteins exemplified above, such as variants of genes and proteins having known nucleotide sequences and amino acid sequences, respectively, so long as the original function thereof, such as respective enzymatic activities in cases of proteins, is maintained. As for variants of genes and proteins, the descriptions concerning variants of a gene encoding a protein having L-methionine/branched-chain amino acid exporter activity and the encoded protein described herein can be similarly applied.

The bacterium as described herein has been modified to overexpress a gene encoding a protein having L-methionine/branched-chain amino acid exporter activity.

The phrase "a protein having L-methionine/branched-chain amino acid exporter activity" can mean a protein that can cause an increase in the extracellular concentration of L-methionine, L-leucine, L-isoleucine, and/or L-valine, for example, all of them, when the bacterium is cultured in a medium. In particular, the phrase "a protein having L-methionine/branched-chain amino acid exporter activity" can mean a protein that can cause the increase of extracellular concentration of L-methionine, L-leucine, L-isoleucine, and L-valine when the bacterium is cultured in a medium containing Met-Met, Ile-Ile, Leu-Leu, and Val-Val dipeptides (Liu Q. et al., YjeH is a novel exporter of L-methionine and branched-chain amino acids in *Escherichia coli*, *Appl. Environ. Microbiol.*, 2015, 81(22):7753-7766). The phrase "a protein having L-methionine/branched-chain amino acid exporter activity" can also mean a protein that can cause the transport of L-methionine, L-leucine, L-isoleucine, and/or L-valine, for example, all of them, outside a bacterial cell when the bacterium is cultured in a medium. In particular, the phrase "a protein having L-methionine/branched-chain amino acid exporter activity" can also mean a protein that can cause the transport of L-methionine, L-leucine, L-isoleucine, and L-valine outside a bacterial cell when the bacterium is cultured in a medium containing Met-Met, Ile-Ile, Leu-Leu, and Val-Val dipeptides (Liu Q. et al., 2015).

The phrase "a protein having L-methionine/branched-chain amino acid exporter activity" can also mean a protein that can confer to a bacterium the resistance to toxic analogs of L-methionine and branched-chain amino acids (abbreviated as BCAAs) such as DL-ethionine, DL-norleucine, and DL-norvaline.

The phrase "a protein having L-methionine/branched-chain amino acid exporter activity" can also mean a protein that can cause, when a bacterium is cultured in a medium, an increase in the extracellular concentration of L-methionine, L-leucine, L-isoleucine, and L-valine or the transport of L-methionine, L-leucine, L-isoleucine, and L-valine outside the bacterial cell, and confer to the bacterium resistance to DL-ethionine, DL-norleucine, and DL-norvaline.

The activity of a protein having L-methionine/branched-chain amino acid exporter activity can be determined using growth inhibition test and/or amino acid export assay. The growth inhibition test can be performed by culturing (that is, growing) a bacterium in a medium containing a structural analog of L-methionine or a branched-chain amino acid such as DL-ethionine, DL-norleucine, and DL-norvaline, and evaluating the cell growth inhibition (Liu Q. et al., 2015). The transport of an amino acid outside a bacterial cell can be determined by, for example, evaluating an amount of the amino acid in the form of a derivative of 2,4-dinitrofluorobenzene (DNFB) in the extracellular and intracellular cell fractions using high-performance liquid chromatography (HPLC) (Liu Q. et al., 2015).

Furthermore, it is known that there are membrane proteins that can confer on a bacterium resistance to target compounds such as, for example, analogs of amino acids (Doroshenko V. et al., YddG from *Escherichia coli* promotes export of aromatic amino acids, *FEMS Microbiol. Lett.*, 2007, 275(2):312-318). Methods for determining the activity of transporter proteins that can confer to a bacterium resistance to a target compound are known, and those methods can be similarly used to determine the activity of a protein having L-methionine/branched-chain amino acid exporter activity, in which, for example, the minimal inhibitory concentration (MIC) is determined for the protein towards the target compound (see, for example, Doroshenko V. et al., 2007; Livshits V. A. et al., Identification and characterization of the new gene rhtA involved in threonine and homoserine efflux in *Escherichia coli*, *Res. Microbiol.*, 2003, 154(2):123-135).

The protein concentration can be determined by the Bradford protein assay or the method of Lowry using bovine serum albumin (BSA) as a standard and a Coomassie dye (Bradford M. M., *Anal. Biochem.*, 1976, 72:248-254; Lowry O. H. et al., *J. Biol. Chem.*, 1951, 193:265-275).

An example of the protein having L-methionine/branched-chain amino acid exporter activity can be a protein having the amino acid sequence shown in SEQ ID NO: 2. The amino acid sequence shown in SEQ ID NO: 2 can be encoded by the nucleotide sequence shown in SEQ ID NO: 1, which corresponds to the yjeH gene native to *E. coli* strain K-12. The yjeH gene native to *E. coli* strain K-12 (GenBank, accession No. NC_000913.3; nucleotide positions: 4369156 to 4370412; Gene ID: 948656) encodes an L-methionine/branched-chain amino acid exporter YjeH (EcoCyc database, ecocyc.org/, accession ID: G7833; UniProtKB/Swiss-Prot database, accession No. P39277; KEGG, Kyoto Encyclopedia of Genes and Genomes, entry No. b4141). The yjeH gene is located between the fxsA gene and the groS gene on the opposite strand on the chromosome of *E. coli* strain K-12. The nucleotide sequence of the yjeH gene (SEQ ID NO: 1) and the amino acid sequence of the YjeH protein (SEQ ID NO: 2) encoded by the yjeH gene are known.

That is, the gene encoding a protein having L-methionine/branched-chain amino acid exporter activity may be a yjeH gene, and the protein having L-methionine/branched-chain amino acid exporter activity may be a YjeH protein. Specifically, the gene encoding a protein having L-methionine/branched-chain amino acid exporter activity, such as a yjeH gene, may be a gene, such as DNA, having the nucleotide sequence of SEQ ID NO: 1, and the protein having L-methionine/branched-chain amino acid exporter activity, such as a YjeH protein, may be a protein having the amino acid sequence of SEQ ID NO: 2. The phrase "a gene or protein has a nucleotide or amino acid sequence" can mean that a gene or protein includes the nucleotide or amino acid sequence among a larger sequence unless otherwise stated, and can also mean that a gene or protein has only the nucleotide or amino acid sequence.

Homologues of the YjeH protein native to different bacterial species belonging to the family Enterobacteriaceae are known, examples of which are described in Table 1.

TABLE 1

Examples of YjeH proteins

| Accession No.* | Organism | Identity** |
| --- | --- | --- |
| CQR83521.1 | *Escherichia coli* (strain K-12) | 100% |
| OZQ55857.1 | *Klebsiella pneumoniae* | 99% |
| OYF34459.1 | *Shigella sonnei* | 99% |
| OYJ35320.1 | *Shigella boydii* | 99% |
| WP_059259351.1 | *Escherichia albertii* | 96% |
| WP_103818667.1 | *Escherichia sp.* ESNIH1 | 84% |
| GAS74125.1 | *Salmonella enterica* | 88% |
| WP_079777245.1 | *Salmonella bongori* | 72% |
| WP_063941667.1 | *Enterobacter cloacae* | 87% |
| WP_089600259.1 | *Enterobacter mori* | 82% |
| WP_044699201.1 | *Citrobacter freundii* | 87% |
| WP_042321353.1 | *Citrobacter farmeri* | 91% |
| WP_110274508.1 | *Klebsiella oxytoca* | 82% |
| CDK73502.1 | *Klebsiella pneumoniae* IS22 | 99% |
| WP_083581956.1 | *Pantoea sesami* | 83% |
| WP_059179910.1 | *Lelliottia amnigena* | 83% |
| WP_045853383.1 | *Raoultella terrigena* | 83% |
| WP_032698341.1 | *Raoultella planticola* | 82% |
| WP_039028410.1 | *Leclercia adecarboxylata* | 84% |
| WP_054179688.1 | *Trabulsiella odontotermitis* | 80% |
| PLA70030.1 | *Leclercia adecarboxylata* | 83% |
| WP_038156337.1 | *Trabulsiella quamensis* | 79% |

TABLE 1-continued

Examples of YjeH proteins

| Accession No.* | Organism | Identity** |
| --- | --- | --- |
| WP_079517063.1 | *Kosakonia oryzae* | 79% |
| WP_035886949.1 | *Kosakonia radicincitans* | 78% |
| WP_048273154.1 | *Pluralibacter gerqoviae* | 78% |
| WP_034920288.1 | *Shimwellia blattae* | 79% |
| WP_035894235.1 | *Kluyvera ascorbata* | 78% |
| WP_062775967.1 | *Kluyvera intermedia* | 78% |
| WP_100777918.1 | *Cedecea lapaqei* | 83% |
| WP_044181175.1 | *Metakosakonia massiliensis* | 78% |
| RDK95757.1 | *Enterobavillus tribolii* | 76% |
| WP_108900379.1 | *Limnobaculum parvum* | 67% |
| WP_034863829.1 | *Enterobacteriacea bacterium* B14 | 69% |

*in the NCBI database (National Center for Biotechnology Information, www.ncbi.nlm-.nih.gov/)
**Identity was calculated with respect to the YjeH protein native to *E. coli* strain K-12 (GenBank:CQR83521.1) using blastp and default settings provided by the NCBI database.

There may be some differences in DNA sequences between the genera, species, or strains of the bacteria belonging to the family Enterobacteriaceae. Therefore, the gene encoding a protein having L-methionine/branched-chain amino acid exporter activity, such as a yjeH gene, is not limited to the gene having the nucleotide sequence shown in SEQ ID NO: 1, but may include genes having variant nucleotide sequences of SEQ ID NO: 1, and encoding variant proteins having L-methionine/branched-chain amino acid exporter activity. Similarly, the protein having L-methionine/branched-chain amino acid exporter activity, such as a YjeH protein, is not limited to the protein having the amino acid sequence shown in SEQ ID NO: 2, but may include proteins having variant amino acid sequences of SEQ ID NO: 2 and having L-methionine/branched-chain amino acid exporter activity. Examples of such variant nucleotide sequences or variant amino acid sequences may include homologues of and artificially modified genes encoding a protein having L-methionine/branched-chain amino acid exporter activity exemplified above or of the protein having L-methionine/branched-chain amino acid exporter activity exemplified above.

The phrase "a variant nucleotide sequence" can mean a nucleotide sequence which encodes a protein having L-methionine/branched-chain amino acid exporter activity, such as the protein having the amino acid sequence shown in SEQ ID NO: 2, using any synonymous amino acid codons according to the standard genetic code table (see, for example, Lewin B., "*Genes VIII*", 2004, Pearson Education, Inc., Upper Saddle River, NJ 07458). Therefore, the gene encoding a protein having L-methionine/branched-chain amino acid exporter activity having the amino acid sequence shown in SEQ ID NO: 2 can be a gene having a variant nucleotide sequence of SEQ ID NO: 1 due to the degeneracy of the genetic code.

The phrase "a variant nucleotide sequence" can also mean a nucleotide sequence that is able to hybridize under stringent conditions with the nucleotide sequence complementary to the sequence shown in SEQ ID NO: 1 or a probe that can be prepared from the nucleotide sequence provided that it encodes a protein that maintains activity or function of the protein having L-methionine/branched-chain amino acid exporter activity having the amino acid sequence shown in SEQ ID NO: 2, or the three-dimensional structure of the protein is not significantly changed relative to the non-modified protein having L-methionine/branched-chain amino acid exporter activity such as, for example, the wild-type protein YjeH native to *E. coli*. "Stringent conditions" can refer to conditions under which a specific hybrid, for example, a hybrid having homology, defined as the parameter "identity" when using the computer program blastn, not less than 70%, not less than 75%, not less than 80%, not less than 85%, not less than 90%, not less than 91%, not less than 92%, not less than 93%, not less than 94%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate) at 60° C., 0.1×SSC, 0.1% SDS at 60° C., or 0.1×SSC, 0.1% SDS at 65° C. Duration of washing can depend on the type of membrane used for the blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1 may also be used. Such a probe can be produced by PCR (polymerase chain reaction; refer to White T. J. et al., The polymerase chain reaction, *Trends Genet.*, 1989, 5:185-189) using oligonucleotides as primers prepared on the basis of the sequence shown in SEQ ID NO: 1 and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after the hybridization can be, for example, 2×SSC, 0.1% SDS at 50° C., 60° C. or 65° C.

The phrase "a variant nucleotide sequence" can also mean a nucleotide sequence that encodes a variant protein.

The phrase "a variant protein" can mean a protein which has a variant amino acid sequence of SEQ ID NO: 2.

The phrase "a variant protein" can specifically mean a protein which has one or more mutations in the sequence as compared with the amino acid sequence shown in SEQ ID NO: 2, whether they are substitutions, deletions, insertions, and/or additions of one or several amino acid residues, but which still maintains the activity or function of the protein having L-methionine/branched-chain amino acid exporter activity having the amino acid sequence shown in SEQ ID NO: 2, or of which the three-dimensional structure of the protein is not significantly changed relative to the non-modified protein having L-methionine/branched-chain amino acid exporter activity, such as the protein having the amino acid sequence shown in SEQ ID NO: 2. The number of changes in the variant protein depends on the position of amino acid residue(s) in the three-dimensional structure of the protein or the type of amino acid residue(s). It can be, but is not strictly limited to, 1 to 100, in another example 1 to 90, in another example 1 to 80, in another example 1 to 70, in another example 1 to 60, in another example 1 to 50, in another example 1 to 40, in another example 1 to 30, in another example 1 to 20, in another example 1 to 15, in another example 1 to 10, and in another example 1 to 5, in SEQ ID NO: 2. This is possible because amino acids can have high homology to one another, so that the activity or function of a protein is not affected by a change between such amino acids, or the three-dimensional structure of a protein cannot be significantly changed relative to the non-modified protein having L-methionine/branched-chain amino acid exporter activity, such as the protein having the amino acid sequence shown in SEQ ID NO: 2, by a change between such amino acids. Therefore, the variant protein may be a protein having an amino acid sequence having a homology, defined as the parameter "identity" when using the computer program blastp, not less than 70%, not less than 75%, not less than 80%, not less than 85%, not less than 90%, not less than 91%, not less than 92%, not less than 93%, not less than 94%, not less than 95%, not less than 96%, not less than 97%, not less than 98%, or not less than 99% with respect to the entire amino acid sequence shown in SEQ ID NO: 2 as long as activity or function of the protein having L-methionine/branched-chain amino acid exporter activity is maintained, or the three-dimensional structure of the protein is not significantly changed relative to the non-modified the protein having L-methionine/branched-chain amino acid exporter activity, such as the protein having the amino acid sequence shown in SEQ ID NO: 2. In this specification, "homology" may mean "identity", which is the identity of amino acid residues. The sequence identity between two sequences is calculated as the ratio of residues matching in the two sequences when aligning the two sequences so as to achieve a maximum alignment with each other.

The exemplary substitution, deletion, insertion, and/or addition of one or several amino acid residues can be a conservative mutation(s). The representative conservative mutation can be a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. In addition, such substitution, deletion, insertion, addition or the like of amino acid residues as mentioned above includes a naturally occurring mutation due to an individual difference of an organism to which the amino acid sequence is native.

The exemplary substitution, deletion, insertion, and/or addition of one or several amino acid residues can also be a non-conservative mutation(s) provided that the mutation(s) is/are compensated by one or more secondary mutation(s) in the different position(s) of amino acids sequence so that activity or function of the variant protein is maintained, or the three-dimensional structure of the protein is not significantly changed relative to the non-modified protein having L-methionine/branched-chain amino acid exporter activity, such as the protein having the amino acid sequence shown in SEQ ID NO: 2.

The calculation of a percent identity of a polypeptide can be carried out using the algorithm blastp. More specifically, the calculation of a percent identity of a polypeptide can be carried out using the algorithm blastp in the default settings of Scoring Parameters (Matrix: BLOSUM62; Gap Costs: Existence=11 Extension=1; Compositional Adjustments: Conditional compositional score matrix adjustment) provided by National Center for Biotechnology Information (NCBI). The calculation of a percent identity of a polynucleotide can be carried out using the algorithm blastn. More specifically, the calculation of a percent identity of a polynucleotide can be carried out using the algorithm blastn in the default settings of Scoring Parameters (Match/Mismatch Scores=1,-2; Gap Costs=Linear) provided by NCBI.

The phrase "a bacterium has been modified to overexpress a gene encoding a protein having L-methionine/branched-chain amino acid exporter activity" can mean that the bacterium has been modified in such a way that in the modified bacterium the total amount and/or the total enzymatic activity of the corresponding gene product such as the protein having L-methionine/branched-chain amino acid exporter activity is increased as compared with (i.e. higher than), or the expression level (i.e. expression amount) of a gene encoding a protein having L-methionine/branched-chain amino acid exporter activity is increased as compared with (i.e. higher than), that observed for a non-modified strain, for example, a wild-type or parental strain. Examples of a non-modified strain that can serve as a reference for the above comparison can include a wild-type strain of a bacterium belonging to the family Enterobacteriaceae such as, for example, the *E. coli* W3110 strain (ATCC 27325), the *E. coli* MG1655 strain (ATCC 47076), and the *P. ananatis* AJ13355 strain (FERM BP-6614).

The total amount and/or the total enzymatic activity of the corresponding gene product such as the protein having L-methionine/branched-chain amino acid exporter activity can be increased by, for example, increasing (i e enhancing) the expression level of said gene, or increasing the activity per molecule (may be referred to as a specific activity) of the protein encoded by said gene, as compared with a non-modified strain, for example, a wild-type or parental strain. An increase in the total amount or the total activity of a protein can be measured as, for example, an increase in the amount or activity of the protein per cell, which may be an average amount or activity of the protein per cell. The bacterium can be modified so that the amount and/or the activity of the protein having L-methionine/branched-chain amino acid exporter activity per cell is increased to 150% or more, 200% or more, or 300% or more, of the amount and/or the activity of a non-modified strain.

The phrase "a bacterium has been modified to overexpress a gene encoding a protein having L-methionine/branched-chain amino acid exporter activity" can also mean that the bacterium has been modified in such a way that in the modified bacterium the expression level (i.e. expression amount) of a gene encoding a protein having L-methionine/branched-chain amino acid exporter activity is enhanced or increased as compared with a non-modified strain, for example, a wild-type or parental strain. Therefore, the phrase "a gene encoding a protein having L-methionine/branched-chain amino acid exporter activity is overexpressed" can be used interchangeably or equivalently to the phrase "expression of a gene encoding a protein having L-methionine/branched-chain amino acid exporter activity is enhanced or increased" or the phrase "the expression level of a gene encoding a protein having L-methionine/branched-chain amino acid exporter activity is enhanced or increased". Furthermore, the phrase "a bacterium has been modified to overexpress a gene encoding a protein having L-methionine/branched-chain amino acid exporter activity" can also mean that the expression level of a gene encoding a protein having L-methionine/branched-chain amino acid exporter activity in the modified bacterium is higher than that observed for a non-modified strain. An increase in the expression level of a gene can be measured as, for example, an increase in the expression level of the gene per cell, which may be an average expression level of the gene per cell. The phrase "the expression level of a gene" or "the expression amount of a gene" can mean, for example, the amount of an expression product of a gene, such as the amount of mRNA of the gene or the amount of the protein encoded by the gene. The bacterium may be modified so that the expression level of the gene encoding a protein having L-methionine/branched-chain amino acid exporter activity per cell is increased to, for example, 150% or more, 200% or more, or 300% or more, of the expression level of the gene encoding a protein having L-methionine/branched-chain amino acid exporter activity in a non-modified strain.

Examples of methods which can be used to overexpress a gene such as the gene encoding a protein having L-methionine/branched-chain amino acid exporter activity include, but are not limited to, a method of increasing the copy number of the gene, such as copy number of the gene in the chromosome and/or in the autonomously replicating vector, such as a plasmid, harbored by the bacterium. The copy number of a gene can be increased by, for example, introducing the gene into the chromosome of the bacterium and/or introducing an autonomously replicating vector containing the gene into the bacterium. Such increasing of the copy number of a gene can be carried out according to genetic engineering methods known to the person of ordinary skill in the art.

Examples of the vectors that can be used for a bacterium belonging to the family Enterobacteriaceae can include, but are not limited to, conditionally-replicated vectors such as, for example, vectors having R6K (oriRγ) origin replication such as, for example, the pAH162 vector and the like, narrow-host-range plasmids such as pMW118/119, pBR322, pUC19 and the like, or broad-host-range plasmids such as RSF1010, RP4 and the like. The gene encoding a protein having L-methionine/branched-chain amino acid exporter activity can also be introduced into the chromosomal DNA of a bacterium by, for example, homologous recombination, Mu-driven integration, or the like. Only one copy, or two or more copies of the gene encoding a protein having L-methionine/branched-chain amino acid exporter activity may be introduced. For example, homologous recombination can be carried out using a nucleotide sequence the multiple copies of which exist in the chromosomal DNA as a target to introduce multiple copies of the gene encoding a protein having L-methionine/branched-chain amino acid exporter activity into the chromosomal DNA. Examples of a nucleotide sequence multiple copies of which exist in the chromosomal DNA can include, but are not limited to, repetitive DNA, and inverted repeats present at the end of a transposable element. In addition, it is possible to incorporate a gene into a transposon and allow it to be transferred to introduce multiple copies of the gene into the chromosomal DNA. A method for intrachromosomal amplification can be used to introduce multiple copies of a gene into the chromosomal DNA. By using Mu-driven transposition, more than 3 copies of the gene can be introduced into the chromosomal DNA of recipient strain in one step (Akhverdyan V. Z. et al., *Biotechnol. (Russian)*, 2007, 3:3-20).

A gene to be introduced into the bacterium as described herein can be ligated downstream from a promoter. The promoter is not particularly limited so long as the chosen promoter can function in the host bacterium, and it may be a promoter native to the host bacterium, or it may be a heterologous promoter. The promoter may be the native promoter of the gene to be introduced, or it may be a promoter of another gene. The phrase "a promoter that can function in a host bacterium" can refer to a promoter that possesses promoter activity in a host bacterium. Specific examples of a promoter that can function in a bacterium belonging to the family Enterobacteriaceae include, but are not limited to, potent promoters exemplified below.

Examples of methods which can be used to overexpress a gene such as the gene encoding a protein having L-methionine/branched-chain amino acid exporter activity also include a method of increasing the expression level of the gene by modification of an expression regulatory region of that gene. Modification of an expression regulatory region of a gene can be employed in combination with an increase in the copy number of the gene. An expression regulatory region of a gene can be modified by, for example, replacing the native expression regulatory region of the gene with a native and/or modified foreign regulatory region(s). The phrase "an expression regulatory region" can be used interchangeably or equivalently with the phrase "an expression regulatory sequence". When the gene encoding a protein having L-methionine/branched-chain amino acid exporter activity is organized in an operon structure in combination with one or more other gene(s), the method which can be used to enhance expression of the gene also includes increasing the expression level of the operon having that gene by modification of an expression regulatory region of the operon, wherein the modification can be carried out by, for example, replacing the native expression regulatory region of the operon with a native and/or modified foreign regulatory region. In this method, the expression of two or more genes, including the gene encoding a protein having L-methionine/branched-chain amino acid exporter, can be enhanced at the same time.

Expression regulatory regions can be exemplified by promoters, enhancers, operators, attenuators and termination signals, anti-termination signals, ribosome-binding sites (RBS) and other expression control elements (e.g., regions to which repressors or activators bind and/or binding sites for transcriptional and translational regulatory proteins, for example, in the transcribed mRNA). Such regulatory regions are described, for example, in known documents (Sambrook J., Fritsch E. F. and Maniatis T., "Molecular Cloning: A Laboratory Manual", 2$^{nd}$ ed., Cold Spring Harbor Laboratory Press (1989); Pfleger B. F. et al., Combinatorial engineering of intergenic regions in operons tunes expression of multiple genes, *Nat. Biotechnol.*, 2006, 24:1027-1032; Mutalik V. K. et al., Precise and reliable gene expression via standard transcription and translation initiation elements, *Nat. Methods*, 2013, 10:354-360). Modifications of an expression regulatory region of a gene can be combined with increasing the copy number of the gene (see, for example, Akhverdyan V. Z. et al., *Appl. Microbiol. Biotechnol.*, 2011, 91:857-871; Tyo K. E. J. et al., *Nature Biotechnol.*, 2009, 27:760-765).

The exemplary promoters suitable for enhancing expression of the gene encoding a protein having L-methionine/branched-chain amino acid exporter activity can be potent promoters. The phrase "a potent promoter" can refer to a promoter that is stronger than the native promoter of the gene encoding a protein having L-methionine/branched-chain amino acid exporter activity. Examples of potent promoters that can function in a bacterium belonging to the family Enterobacteriaceae can include, but are not limited to, lac promoter, trp promoter, trc promoter, tac promoter, tet promoter, araBAD promoter, rpoH promoter, msrA promoter, Pm1 promoter (derived from the genus *Bifidobacterium*), and $P_R$ or $P_L$ promoters of lambda (λ) phage. As a potent promoter, a highly active variant of an existing promoter may also be obtained by using various reporter genes. For example, by making the −35 and −10 regions in a promoter region closer to a consensus sequence, the strength of the promoter can be enhanced (WO0018935 A1). The strength of a promoter can be defined by the frequency of initiation acts of RNA synthesis. Examples of the method for evaluating the strength of a promoter and examples of strong promoters are described in the paper of Goldstein M. A. et al. (Prokaryotic promoters in biotechnology, *Biotechnol. Annu. Rev.*, 1995, 1:105-128) and so forth. Potent promoters providing a high level of gene expression in a bacterium belonging to the family Enterobacteriaceae can be used. Alternatively, the effect of a promoter can be enhanced by, for example, introducing a mutation into the promoter region of the gene encoding a protein having L-methionine/branched-chain amino acid exporter activity to obtain a stronger promoter function, thus resulting in the increased transcription level of the gene encoding a protein having L-methionine/branched-chain amino acid exporter activity located downstream of the promoter. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. Hence, these portions can be examples of expression regulatory regions of a gene. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629).

Examples of methods which can be used to inactivate a gene include a method of modifying a gene such that the modified gene encodes a completely inactive or non-functional protein as compared with the gene encoding a native protein, or the modified DNA region is unable to naturally express the gene due to deletion of a part of the gene or deletion of the entire gene, replacement of one base or more to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an expression regulatory region such as promoters, enhancers, operators, attenuators and termination signals, anti-termination signals, ribosome-binding sites (RBS), and other expression control elements. Inactivation of the gene can also be performed, for example, by conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al., *Proc. Natl. Acad. Sci. USA*, 2000, 97(11):5978-5983; Datsenko K. A. and Wanner B. L., *Proc. Natl. Acad. Sci. USA*, 2000, 97(12):6640-6645; Zhang Y. et al., *Nature Genet.*, 1998, 20:123-128) based on "Red/ET-driven integration" or "λRed/ET-mediated integration".

The copy number of a gene or the presence or absence of a gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the persons skilled in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, DC, ASM Press (2009).

Any methods for manipulation with recombinant DNA can be used including conventional methods such as, for example, transformation, transfection, infection, conjugation, and mobilization. Transformation, transfection, infection, conjugation or mobilization of a bacterium with the DNA encoding a protein can impart to the bacterium the ability to synthesize the protein encoded by the DNA. Methods of transformation, transfection, infection, conjugation, and mobilization include any known methods. For example, a method of treating recipient cells with calcium chloride so as to increase permeability of the cells of *E. coli* K-12 to DNA has been reported for efficient DNA transformation and transfection (Mandel M. and Higa A., Calcium-dependent bacteriophage DNA infection, *J. Mol. Biol.*, 1970, 53:159-162). Methods of specialized and/or generalized transduction were described (Morse M. L. et al., Transduction in *Escherichia coli* K-12, *Genetics*, 1956, 41(1):142-156; Miller J. H., *Experiments in Molecular Genetics*. Cold Spring Harbor, N.Y.: Cold Spring Harbor La. Press, 1972). Other methods for random and/or targeted integration of DNA into the host microorganism can be applied, for example, "Mu-driven integration/amplification" (Akhverdyan et al., *Appl. Microbiol. Biotechnol.*, 2011, 91:857-871), "Red/ET-driven integration" or "λRed/ET-mediated integration" (Datsenko K. A. and Wanner B. L., *Proc. Natl. Acad. Sci. USA* 2000, 97(12):6640-45; Zhang Y., et al., *Nature Genet.*, 1998, 20:123-128). Moreover, for multiple insertions of desired genes in addition to Mu-driven replicative transposition (Akhverdyan et al., *Appl. Microbiol. Biotechnol.*, 2011, 91:857-871) and chemically inducible chromosomal evolution based on recA-dependent homologous recombination resulted in an amplification of desired genes (Tyo K. E. J. et al., *Nature Biotechnol.*, 2009, 27:760-765), another methods can be used, which utilize different combinations of transposition, site-specific and/or homologous Red/ET-mediated recombinations, and/or P1-mediated generalized transduction (see, for example, Minaeva N. et al., *BMC Biotechnology*, 2008, 8:63; Koma D. et al., *Appl. Microbiol. Biotechnol.*, 2012, 93(2):815-829).

Since the nucleotide sequence of the gene encoding a protein having L-methionine/branched-chain amino acid exporter activity native to bacterial species such as *E. coli* and other ones, examples of which are listed in Table 1, and the amino acid sequence of the protein encoded by this gene have already been elucidated (see above), the gene native to such a bacterial species or a variant nucleotide sequence thereof can be obtained by cloning from the bacterial species by PCR utilizing DNA of the bacterial species and oligonucleotide primers prepared based on the nucleotide sequence of the yjeH gene native to the bacterial species; or a mutagenesis method of treating a DNA containing the yjeH gene, in vitro, for example, with hydroxylamine, or a mutagenesis method of treating the bacterial species harboring the yjeH gene with ultraviolet (UV) irradiation or a mutating agent such as N-methyl-N'-nitro-N-nitrosoguanidine (NTG) and nitrous acid usually used for the such treatment; or chemical synthesis as a full-length gene structure. Genes encoding a protein having L-methionine/branched-chain amino acid exporter activity native to any other organisms, including other bacterial species, or a variant nucleotide sequence thereof can be obtained in a similar manner The phrase "native to" in reference to a protein or a nucleic acid can mean that the protein or the nucleic acid is native to a particular organism such as, for example, mammals, plants, insects, bacteria, and viruses. That is, a protein or a nucleic acid native to a particular organism can mean the protein or the nucleic acid, respectively, that exists naturally in the organism. A protein or a nucleic acid native to a particular organism can be isolated from the organism and sequenced using means known to the one of ordinary skill in the art. Moreover, as the amino acid sequence or the nucleotide sequence of a protein or nucleic acid, respectively, isolated from an organism in which the protein or nucleic acid exists, can easy be determined, the phrase "native to" in reference to a protein or a nucleic acid can also refer to a protein or a nucleic acid that can be obtained using any means, for example, a genetic engineering technique, including recombinant DNA technology, or a chemical synthesis method, or the like, so long as the amino acid sequence of the protein or the nucleotide sequence of the nucleic acid thus obtained is identical to the amino acid sequence of the protein or the nucleotide sequence of the nucleic acid that exists naturally in, is expressed naturally in, and/or is produced naturally by the organism. The phrase "a protein" can refer to, but is not limited to, any of peptides, oligopeptides, polypeptides, proteins, enzymes, and so forth. The phrase "a nucleic acid" can refer to deoxyribonucleic acid (DNA) or ribonucleic acid (RNA), and can specifically refer to, but are not limited to, any of expression regulatory sequences, including promoters, attenuators, terminators, and the like, genes, intergenic sequences, nucleotide sequences encoding signal peptides, pro-moieties of proteins, artificial amino acid sequences, and so forth. For example, a gene can particularly be DNA. Specific examples of amino acid sequences and nucleotide sequences, and homologues thereof native to various species are described herein, and these examples include a protein having the amino acid sequences shown in SEQ ID NO: 2, which is native to the bacterium of the species *E. coli*, which can be encoded by the gene having the nucleotide sequence shown in SEQ ID NO: 1.

The phrase "non-modified", which can be used interchangeably or equivalently to the phrases "native", "natural", and "wild-type", in reference to a gene (for example, "a non-modified gene") and a protein (for example, "a non-modified protein"), can mean, respectively, a native gene and a native protein that exist naturally in, are expressed naturally in, and/or are produced naturally by an organism, specifically a non-modified strain of a bacterium. Examples of such an organism can include any organisms having the corresponding gene or protein, and specific examples thereof can include, for example, the E. coli W3110 strain, E. coli MG1655 strain, P. ananatis 13355 strain. A non-modified gene can encode a non-modified protein.

The bacterium can have, in addition to the properties already mentioned, other specific properties such as various nutrient requirements, drug resistance, drug sensitivity, and drug dependence, without departing from the scope of the present invention.

2. Method

The method of producing a basic L-amino acid using the bacterium as described herein includes the steps of cultivating (also called culturing) the bacterium in a culture medium to allow the basic L-amino acid to be produced, excreted or secreted, and/or accumulated in the culture medium or in cells of the bacterium, or both, and collecting the basic L-amino acid from the culture medium and/or the cells. The method may further include, optionally, the step of purifying the basic L-amino acid from the culture medium and/or the cells. The basic L-amino acid can be produced in such a form as described above. The basic L-amino acid can be produced particularly in a free form or as a salt thereof, or as a mixture of them. For example, sodium, potassium, ammonium, and the like salts or an inner salt such as zwitterion of the basic L-amino acid can be produced by the method. This is possible as amino acids can react under fermentation conditions with each other or a neutralizing agent such as an inorganic or organic acidic or alkaline substance in a typical acid-base neutralization reaction to form a salt that is the chemical feature of amino acids which is apparent to the person skilled in the art. Specifically, a monochlorhydrate salt of L-arginine (L-arginine×HCl) or L-lysine (L-lysine×HCl) can be produced by the method.

The cultivation of the bacterium, and collection and, optionally, purification of the basic L-amino acid from the medium and the like may be performed in a manner similar to the conventional fermentation methods wherein an L-amino acid is produced using a microorganism. That is, the cultivation of the bacterium, and collection and purification of the basic L-amino acid from the medium and the like may be performed by applying the conditions that are suitable for the cultivation of the bacterium, and appropriate for the collection and purification of an L-amino acid, which conditions are well-known to the persons of ordinary skill in the art.

The culture medium can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolysates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as of soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, thiosulfate, sulfide, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, vitamin B12, required substances, for example, organic nutrients such as nucleic acids such as adenine and RNA, amino acids, peptone, casamino acid, yeast extract, and the like may be present in appropriate, even if trace, amounts. Other than these, small amounts of calcium phosphate, iron ions, manganese ions, and so forth may be added, if necessary.

Cultivation can be performed under the conditions suitable for cultivating a bacterium chosen for the use in the method as described herein. For example, the cultivation can be performed under aerobic conditions for from 16 to 72 hours or for from 16 to 24 hours, the culture temperature during cultivation can be controlled within from 30 to 45° C. or within from 30 to 37° C., and the pH can be adjusted between 5 and 8 or between 6 and 7.5. The pH can be adjusted using an inorganic or organic acidic or alkaline substance such as urea, calcium carbonate, or ammonia gas.

After cultivation, the basic L-amino acid can be collected from the culture medium. Specifically, the basic L-amino acid present outside of cells can be collected from the culture medium. Also, after cultivation, the basic L-amino acid can be collected from cells of the bacterium. Specifically, the cells can be disrupted, a supernatant can be obtained by removing solids such as the cells and the cell-disrupted suspension (so-called cell debris), and then the basic L-amino acid can be collected from the supernatant. Disruption of the cells can be performed using, for example, methods that are well-known in the art, such as ultrasonic lysis using high frequency sound waves, or the like. Removal of solids can be performed by, for example, centrifugation or membrane filtration. Collection of the basic L-amino acid from the culture medium or the supernatant etc. can be performed using, for example, conventional techniques such as concentration, crystallization, ion-exchange chromatography, medium or high pressure liquid chromatography, or a combination of these.

EXAMPLES

The present invention will be more precisely explained below with reference to the following non-limiting Examples.

Example 1. Construction of E. coli MG1655-Pn1p8-yjeH (Cm$^R$) Strain 1.1 Construction of E. coli MG1655-Pn1p8-yjeH (Cm$^R$) Strain The E. coli MG1655 strain (ATCC 47076) containing the pKD46 plasmid having a temperature-sensitive replication origin was used. The pKD46 plasmid (Datsenko K. A. and Wanner B. L., One-step inactivation of chromosomal genes in Escherichia coli K-12 using PCR products, Proc. Natl. Acad. Sci. USA, 2000, 97(12):6640-6645) includes a 2,154 nucleotides DNA fragment of phage λ (nucleotide positions from 31088 to 33241, GenBank accession No.: J02459), and contains genes of the λRed homologous recombination system (gamma, beta, and exo genes) under the control of the arabinose-inducible $P_{araB}$ promoter. The pKD46 plasmid is necessary for integration of a PCR-product into the chromosome of the *E. coli* MG1655 strain. The *E. coli* MG1655 strain containing the recombinant plasmid pKD46 can be obtained from the *E. coli* Genetic Stock Center, Yale University, New Haven, USA (Accession No. CGSC7669).

Electrocompetent cells were prepared as follows: the *E. coli* MG1655/pKD46 strain was cultured in an LB liquid culture medium (Sambrook J. and Russell D. W., Molecular Cloning: A Laboratory Manual ($3^{rd}$ ed.), Cold Spring Harbor Laboratory Press, 2001) overnight. Then, 1 mL of the cultured medium was inoculated to 100 mL of an LB liquid culture medium containing isopropyl arabinose and ampicillin at final concentrations of 50 mM and 50 mg/L, respectively, and the cells were cultured at 37° C. for 2 hours with shaking (250 rpm). The microbial cells were collected and washed three times with ice cold 10% glycerol to obtain competent cells. An amplified λattL-$Cm^R$-λattR-Pn1p8 fragment (Example 1.2 below) was purified using Wizard PCR Prep DNA Purification System (Promega) and introduced into the competent cells using an electroporation method. The cells were cultured in the SOC culture medium (Sambrook J. and Russell D. W., Molecular Cloning: A Laboratory Manual ($3^{rd}$ ed.), Cold Spring Harbor Laboratory Press, 2001) for 2 hours, then cultivated for 18-24 hours at 37° C. on L-agar plates containing 25 mg/L of chloramphenicol (Cm). Emerging colonies were refined in the same culture medium. Then, PCR reaction was carried out using the primers P1 (SEQ ID NO: 3) and P2 (SEQ ID NO: 4) to confirm that the promoter region of yjeH gene was substituted with the fragment λattL-$Cm^R$-λattR-Pn1p8 on the chromosome. Thus, the *E. coli* MG1655 Pn1p8-yjeH ($Cm^R$) strain was obtained.

1.2. Construction of Fragment λattL-$Cm^R$-λattR-Pn1p8

Fragment λattL-$Cm^R$-λattR-Pn1p8 was constructed as follows. A PCR was carried out using pMW-attL-$Cm^R$-attR-Pn1p8 plasmid (SEQ ID NO: 5) as a template, the primers P3 (SEQ ID NO: 6) and P4 (SEQ ID NO: 7), and Prime Star polymerase (Takara Bio Inc.). A reaction solution was prepared according to the composition attached to the kit, and DNA was amplified through 30 cycles at 98° C. for 10 seconds, 55° C. for 5 seconds and 72° C. for 1 minute per kbp. As a result, the fragment λattL-$Cm^R$-λattR-Pn1p8 having a recombinant sequence of promoter region of yjeH gene and regions complementary to the region adjacent to the yjeH gene at both termini was obtained.

Example 2. Construction of *E. coli* L-Ornithine-Producing Strain

An *E. coli* L-ornithine-producing strain was obtained from *E. coli* L-arginine-producing strain 382i1vA+ by inactivation of ornithine carbamoyltransferase encoded by argF and argI genes. The strain 382i1vA+ was obtained from the L-arginine-producing strain 382 (VKPM B-7926, EP1170358 A1) by P1-transduction of the wild-type i1vA gene from *E. coli* K-12 strain.

2.1. Inactivation of the argF Gene

A strain in which the argF gene was deleted was constructed by the method initially developed by Datsenko K. A. and Wanner B. L. called "λRed/ET-mediated integration" (Datsenko K. A. and Wanner B. L., One-step inactivation of chromosomal genes in *Escherichia coli* K-12 using PCR products, *Proc. Natl. Acad. Sci. USA*, 2000, 97(12):6640-6645). A DNA fragment containing the kanamycin resistance marker ($Km^R$) was obtained by PCR using primers P5 (SEQ ID NO: 8) and P6 (SEQ ID NO: 9) and the pMW118-attL-Km-attR plasmid as the template (WO2011043485 A1). Primer P5 contains both a region complementary to the region located at the 5'-end of the argF gene and a region complementary to the attR region. Primer P6 contains both a region complementary to the region located at the 3'-end of the argF gene and a region complementary to the attL region. The conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

The PCR-product obtained (approximately 1.6 kbp) was purified using Wizard PCR Prep DNA Purification System (Promega) and integrated into the chromosome of the *E. coli* MG1655 (ATCC 47076) strain by the λRed-mediated integration as described in Example 1 using kanamycin (Km) instead of chloramphenicol as a selective marker to replace the native argF gene. Thus, the *E. coli* MG1655ΔargF::$Km^R$ strain was obtained.

2.2. Inactivation of the argI Gene

A strain in which the argI gene was deleted was constructed by the method initially developed by Datsenko K. A. and Wanner B. L. called "λRed/ET-mediated integration" (Datsenko K. A. and Wanner B. L., One-step inactivation of chromosomal genes in *Escherichia coli* K-12 using PCR products, *Proc. Natl. Acad. Sci. USA*, 2000, 97(12):6640-6645). A DNA fragment containing the λattL-$Cm^R$-λattR cassette was obtained by PCR using primers P7 (SEQ ID NO: 10) and P8 (SEQ ID NO: 11) and the pMW118-attL-Cm-attR plasmid as the template (WO2005010175 A1). Primer P7 contains both a region complementary to the region located at the 5'-end of the argI gene and a region complementary to the attR region. Primer P8 contains both a region complementary to the region located at the 3'-end of the argI gene and a region complementary to the attL region. The conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

The obtained PCR product (approximately 1.6 kbp) was purified using Wizard PCR Prep DNA Purification System (Promega) and integrated into the chromosome of the *E. coli* MG1655 ATCC 47076) strain by the λRed-mediated integration as described in Example 1 to replace the native argI gene. Thus, the *E. coli* MG1655ΔargI::$Cm^R$ strain was obtained.

2.3. Construction of *E. coli* Strain Having Inactivated the argI and argF Genes To obtain an *E. coli* L-ornithine-producing strain, DNA fragments from the chromosomes of the obtained *E. coli* MG1655ΔargF::$Km^R$ (Example 2.1) and *E. coli* MG1655ΔargI::$Cm^R$ (Example 2.2) strains were consecutively transferred to the L-arginine-producing *E. coli* strain 382i1vA+ by P1-transductions to obtain the *E. coli* 382i1vA+ΔargI::$Cm^R$ ΔargF::$Km^R$ strain.

The $Cm^R$- and $Km^R$-markers were eliminated simultaneously using the pMW-Int/Xis helper plasmid (WO2005010175 A1) which was electroporated into the selected plasmid-less integrants using electroporation as described in Example 1 for the electroporation of the PCR-generated DNA fragment. After electroporation, cells were plated onto L-agar containing 0.5% glucose and ampicillin (150 mg/L), and incubated at 30° C. overnight to induce synthesis of the Int/Xis proteins. The grown clones were replica-plated on L-agar with and without chloramphenicol and kanamycin to select the Cm$^S$ and Km$^S$ (chloramphenicol and kanamycin-sensitive) variants. Thus, the E. coli 382i1vA$^+$ΔargI ΔargF strain was obtained.

Example 3. Production of L-Ornithine Using E. coli 382i1vA$^+$ΔargI ΔargF Pn1p8-yjeH (Cm$^R$) Strain To test the effect as a result of enhanced expression of the yjeH gene on L-ornithine production, a DNA fragment from the chromosome of the obtained MG1655 Pn1p8-yjeH (Cm$^R$) (Example 1) was transferred to the L-ornithine-producing E. coli strain 382i1vA$^+$ΔargI ΔargF (Example 2.3) by P1-transduction to obtain the E. coli 382i1vA$^+$ΔargI ΔargF Pn1p8-yjeH (Cm$^R$) strain.

The L-ornithine production was evaluated as follows: E. coli strains 382i1vA$^+$Δarg/ΔargF and 382i1vA$^+$ΔargI ΔargF Pn1p8-yjeH (Cm$^R$) were each cultivated with shaking (220 rpm) at 37° C. for 18 hours in 3 mL of nutrient broth (LB medium). Then, 0.3 mL of the obtained cultures was inoculated into 2 mL of the fermentation medium shown in Table 2 using 20×200-mm test tubes and cultivated at 32° C. for 48 hours on a rotary shaker to an OD$_{540}$ of approximately 38 until glucose was fully consumed.

After the cultivation, the amount of L-ornithine which accumulated in the medium was determined by paper chromatography using a mobile phase of butan-1-ol:acetic acid:water=4:1:1 (v/v). A solution of ninhydrin (2%) in acetone was used as a visualizing reagent. A spot containing L-ornithine was cut out, L-ornithine was eluted with a 0.5% water solution of CdCl$_2$, and the amount of L-ornithine was estimated spectrophotometrically at 540 nm.

TABLE 2

| Composition of fermentation medium | |
| --- | --- |
| Component | Final concentration (g/L) |
| Glucose | 48.0 |
| (NH$_4$)$_2$SO$_4$ | 35.0 |
| KH$_2$PO$_4$ | 2.0 |
| MgSO$_4$ × 7H$_2$O | 1.0 |
| Thiamine-HCl | 0.0002 |
| Yeast extract | 1.0 |
| L-Arginine | 0.1 |
| CaCO$_3$ | 5.0 |

Glucose and magnesium sulfate were sterilized separately. CaCO$_3$ was dry-heat sterilized at 180° C. for 2 hours. The pH was adjusted to 7.0 with KOH solution.

The results of eight independent test tube fermentations (as average values) are shown in Table 3. As shown in Table 3, the modified E. coli 382i1vA$^+$ΔargI ΔargF Pn1p8-yjeH (Cm$^R$) strain was able to produce and accumulate a higher amount of L-ornithine as compared with the parent E. coli 382i1vA$^+$ΔargI ΔargF strain.

TABLE 3

| Production of L-ornithine | |
| --- | --- |
| Strain | L-ornithine, g/L |
| E. coli 382ilvA$^+$ΔargI ΔargF (control) | 1.9 |
| E. coli 382ilvA$^+$ΔargI ΔargF Pnlp8-yjeH (Cm$^R$) | 10.1 |

Example 4. Production of L-Citrulline Using E. coli 382i1vA$^+$ΔargG Pn1p8-yjeH (Cm$^R$) Strain 4.1. Construction of E. coli L-Citrulline-Producing Strain An E. coli L-citrulline-producing strain was obtained from E. coli L-arginine-producing strain 382i1vA$^+$ (Example 2) by inactivation of argininosuccinate synthetase encoded by argG gene by the method initially developed by Datsenko K. A. and Wanner B. L. called "λRed/ET-mediated integration" (Datsenko K. A. and Wanner B. L., One-step inactivation of chromosomal genes in Escherichia coli K-12 using PCR products, Proc. Natl. Acad. Sci. USA, 2000, 97(12):6640-6645). According to this procedure, the PCR-primers P9 (SEQ ID NO: 12) and P10 (SEQ ID NO: 13) homologous to both the region adjacent to the argG gene and the gene which confers antibiotic resistance in the template plasmid were constructed. The plasmid pMW118-λattL-Cm-λattR (WO2005010175 A1) was used as the template in the PCR-reaction. The Cm$^R$-marker was eliminated using the pMW-Int/Xis helper plasmid (WO2005010175 A1) as described in Example 2.3. Thus, the E. coli 382i1vA$^+$ΔargG strain was obtained. The strain 382i1vA$^+$ was obtained as described in Example 2.

4.2. Production of L-Citrulline

To test the effect from enhanced expression of the yjeH gene on L-citrulline production, a DNA fragment from the chromosome of the obtained MG1655 Pn1p8-yjeH (Cm$^R$) (Example 1) was transferred to the L-citrulline-producing E. coli strain 382i1vA$^+$ΔargG by P1-transduction to obtain the E. coli 382i1vA$^+$ΔargG Pn1p8-yjeH (Cm$^R$) strain.

E. coli strains 382i1vA$^+$ΔargG and 382i1vA$^+$ΔargG Pn1p8-yjeH (Cm$^R$) were each cultivated with shaking at 37° C. for 18 hours in 3 mL of nutrient broth, and 0.3 mL of the obtained cultures were inoculated into 2 mL of a fermentation medium shown in Table 2 in 20×200-mm test tubes and cultivated at 32° C. for 48 hours on a rotary shaker. After the cultivation, the amount of L-citrulline which accumulated in the medium was estimated as described in Example 3.

The results of eight independent test tube fermentations (as average values) are shown in Table 4. As shown in Table 4, the modified E. coli 382i1vA$^+$ΔargG Pn1p8-yjeH (Cm$^R$) strain was able to produce and accumulate a higher amount of L-citrulline as compared with the parent E. coli 382i1vA$^+$ ΔargG strain.

TABLE 4

| Production of L-citrulline | |
| --- | --- |
| Strain | L-citrulline, g/L |
| E. coli 382ilvA$^+$ΔargG (control) | 3.7 |
| E. coli 382ilvA$^+$ΔargG Pnlp8-yjeH (Cm$^R$) | 9.4 |

Example 5. Production of L-Arginine Using E. coli 382i1vA$^+$Pn1p8-yjeH (Cm$^R$) Strain To test the effect from enhanced expression of the yjeH gene on L-arginine production, a DNA fragment from the chromosome of the obtained MG1655 Pn1p8-yjeH (Cm$^R$) (Example 1) is transferred to the L-arginine-producing E. coli strain 382i1vA$^+$ (Example 2) by P1-transduction to obtain the E. coli 382i1vA$^+$ Pn1p8-yjeH (Cm$^R$) strain.

E. coli strains 382i1vA$^+$ and 382i1vA$^+$ Pn1p8-yjeH (Cm$^R$) are each cultivated with shaking at 37° C. for 18 hours in 3 mL of nutrient broth, and 0.3 mL of the obtained cultures are inoculated into 2 mL of a fermentation medium in 20×200-mm test tubes and cultivated at 32° C. for 48 hours on a rotary shaker. Composition of the fermentation medium is the same as described in Example 3. After the cultivation, the amount of L-arginine which accumulated in the medium is estimated as described in Example 3.

Example 6. Production of L-Histidine Using E. coli EA92 Pn1p8-yjeH (Cm$^R$) Strain To test the effect from enhanced expression of the yjeH gene on L-histidine production, a DNA fragment from the chromosome of the obtained MG1655 Pn1p8-yjeH (Cm$^R$) (Example 1) was transferred to the L-histidine-producing E. coli strain EA92 by P1-transduction to obtain the E. coli EA92 Pn1p8-yjeH (Cm$^R$). The strain EA92 was obtained as described in the Auxiliary example.

The E. coli strains EA92 and EA92 Pn1p8-yjeH (Cm$^R$) from stock tube (stored in a mixture of 25% glycerol and 0.9% NaCl at −70° C.) were each plated on L-agar plates supplemented with antibiotic, if necessary, and grown at 37° C. overnight. Cells from about 0.1 cm$^2$ of plate surface were inoculated into LB liquid culture medium (5 mL) and cultivated for 20 hours at 30° C. at 240 rpm. Then, 0.1 mL of obtained cultures was each inoculated to 2 mL of LB liquid culture medium and grown at 30° C. at 240 rpm to OD (600 nm) 0.6 to obtain seed culture. Then, 0.1 mL of the seed culture was inoculated into 2 mL of the fermentation medium shown in Table 5 using test tubes having a 23 mm internal diameter, all test tubes were 200 mm long, to initiate cultivation. The cultivation was carried out at 32° C. with agitation at 240 rpm for 65 hours.

TABLE 5

Composition of fermentation medium

| Component | Final concentration (g/L) |
|---|---|
| Glucose | 50.0 |
| Mameno* | 0.2 (as the amount of nitrogen) |
| L-aspartate | 1.0 |
| (NH$_4$)$_2$SO$_4$ | 18.0 |
| KCl | 1.0 |
| KH$_2$PO$_4$ | 0.5 |
| MgSO$_4$ × 7H$_2$O | 0.4 |
| FeSO$_4$ × 7H$_2$O | 0.02 |
| MnSO$_4$ × 5H$_2$O | 0.02 |
| ZnSO$_4$ × 7H$_2$O | 0.02 |
| Adenosine | 0.2 |
| Thiamine-HCl | 0.001 |
| Betaine | 2.0 |
| CaCO$_3$ | 60.0 |

*Mameno is a soybean meal hydrolysate (Ajinomoto Co, Inc.).
Glucose, MgSO$_4$ × 7H$_2$O, betaine and CaCO$_3$ were sterilized separately. The pH was adjusted to 6.0 by 6M KOH before sterilization.

After cultivation, accumulated L-histidine was measured using thin-layer chromatography (TLC). TLC plates (10×20 cm) were coated with 0.11 mm layers of Sorbfil silica gel containing non-fluorescent indicator (Sorbpolymer, Krasnodar, Russian Federation). Samples were applied to the plates with the Camag Linomat 5 sample applicator. The Sorbfil plates were developed using a mobile phase consisting of iso-propanol:acetone:25% aqueous ammonia:water=6:6:1.5:1 (v/v). A solution of ninhydrin (1%, w/v) in acetone was used as the visualizing reagent. After development, plates were dried and scanned with the Camag TLC Scanner 3 in absorbance mode with detection at 520 nm using winCATS software (version 1.4.2).

The results of three independent test tube fermentations (as average values) are shown in Table 6. As shown in Table 6, the modified E. coli EA92 Pn1p8-yjeH (Cm$^R$) strain was able to accumulate a higher amount of L-histidine as compared with the parent E. coli EA92 strain.

TABLE 6

Production of L-histidine

| Strain | L-histidine, g/L |
|---|---|
| E. coli EA92 (control) | 4.9 |
| E. coli EA92 Pn1p8-yjeH (Cm$^R$) | 7.9 |

Example 7. Production of L-Lysine Using E. coli WC196LC Pn1p8-yjeH (Cm$^R$)/pCABD2 Strain The E. coli L-lysine-producing strain WC196LC (FERM BP-11027) was transformed with a pCABD2 plasmid for lysine production (International Patent Publications WO95/16042 and WO01/53459), which carries dapA, dapB, lysC and ddh genes, by a conventional method, to thereby yield the WC196LC/pCABD2 strain. The plasmid pCABD2 contains a mutant dapA gene derived from E. coli and encoding dihydrodipicolinate synthase that has a mutation for desensitization to the feedback inhibition by L-lysine, a mutant lysC gene derived from E. coli and encoding aspartokinase III that has a mutation for desensitization to the feedback inhibition by L-lysine, the dapB gene derived from E. coli and encoding dihydrodipicolinate reductase, and the ddh gene derived from Brevibacterium lactofermentum and encoding diaminopimelate dehydrogenase (International Patent Publications WO95/16042 and WO01/53459).

To test the effect from enhanced expression of the yjeH gene on L-lysine production, a DNA-fragment from the chromosome of the obtained E. coli MG1655 Pn1p8-yjeH (Cm$^R$) (Example 1) was transferred to the E. coli L-lysine-producing strain WC196LC/pCABD2 by P1-transduction to obtain the E. coli WC196LC Pn1p8-yjeH (Cm$^R$)/pCABD2 strain.

The E. coli strains WC196LC/pCABD2 and WC196LC Pn1p8-yjeH (Cm$^R$)/pCABD2 were each cultivated with shaking at 37° C. for 18 hours in 3 mL of nutrient broth. Then, 0.3 mL of each of the obtained cultures was inoculated into 2 mL of a fermentation medium shown in Table 2 with addition of 30 mg/L streptomycin in 20×200-mm test tubes and cultivated at 34° C. for 48 hours on a rotary shaker (240 rpm).

After the cultivation, the amount of L-lysine which accumulated in the medium was estimated as described in Example 3.

The results of eight independent test tube fermentations (as average values) are shown in Table 7. As shown in Table 7, the modified E. coli WC196LC Pn1p8-yjeH (Cm$^R$)/pCABD2 strain was able to accumulate a higher amount of L-lysine as compared with the parent E. coli WC196LC/pCABD2 strain.

TABLE 7

Production of L-lysine

| Strain | L-lysine, g/L |
|---|---|
| E. coli WC196LC/pCABD2 | 9.4 |
| E. coli WC196LCPnlp8-yjeH (Cm$^R$)/pCABD2 | 13.0 |

Auxiliary Example

Construction of E. coli EA92 Strain

An E. coli EA92 strain was constructed on the basis of the E. coli EA83 L-histidine-producing strain (MG1655 rph$^+$ ilvG15-[ΔpurR P$_{his}$-ΔhisL' hisG$^{E271K}$DCBHAFI]-[(IS5.11)::(λ-attB)P$_{tac21}$-purA pitA$^-$]-[(λ-attB) P$_L$-purH]) (Malykh E. A. et al., Specific features of L-histidine production by Escherichia coli concerned with feedback control of AICAR formation and inorganic phosphate/metal transport, Microb. Cell Fact., 2018, 17(1):42). The EA83 strain was modified to overexpress aspC gene, to thereby construct the EA92 strain.

In detail, the upstream region of aspC gene was modified by the replacement of a native regulatory region with λ-phage P$_L$ promoter using λRed recombination system (Datsenko and Wanner, 2000). The primers P11 (SEQ ID NO: 14) and P12 (SEQ ID NO: 15) were used to construct a PCR fragment for λRed recombination that harbors an excisable cat marker and the nucleotide sequences homologous to a regulatory region of the aspC gene. The presence of the P$_L$ promoter introduced into the chromosome was confirmed by PCR using the primers P13 (SEQ ID NO: 16) and P14 (SEQ ID NO: 17). Thus, the E. coli strain MG1655 cat-P$_L$-aspC was constructed. This strain was used as a donor to transfer the cat-P$_L$-aspC expression cassette into the chromosome of EA83 using the standard P1 transduction method (Moore S. D., Assembling new Escherichia coli strains by P1-duction, Methods Mol. Biol., 2011, 765:155-169). The excisable chloramphenicol resistance marker (CmR$^{ex}$) was eliminated from the E. coli chromosome using the Xis/Int site-specific recombination system with the use of pMWts-λInt/Xis helper plasmid (Minaeva N. I. et al., 2008). Thus, the E. coli EA92 strain was constructed.

While the invention has been described in detail with reference to exemplary embodiments thereof, it will be apparent to the one of ordinary skill in the art that various changes can be made, and equivalents employed, without departing from the scope of the invention.

INDUSTRIAL APPLICABILITY

The method of the present invention is useful for the production of a basic L-amino acid such as, for example, L-ornithine L-citrulline, L-arginine, L-histidine, and L-lysine by fermentation of a bacterium.

The invention claimed is:

1. A method for producing a basic L-amino acid comprising:
   (i) cultivating a basic L-amino acid producing bacterium belonging to the family Enterobacteriaceae in a culture medium to produce and accumulate the basic L-amino acid in the culture medium or cells of the bacterium, or both, and
   (ii) collecting the basic L-amino acid from the culture medium or the cells, or both,
   wherein said bacterium has been modified to overexpress a DNA encoding a protein having L-methionine/branched chain amino acid exporter activity, and
   wherein said protein having L-methionine/branched chain amino acid exporter activity is selected from the group consisting of:
   (A) a YjeH protein,
   (B) a protein comprising the amino acid sequence set forth in SEQ ID NO: 2,
   (C) a protein comprising the amino acid sequence set forth in SEQ ID NO: 2, but which consists of substitution, deletion, insertion, and/or addition of 1 to 40 amino acid residues, and wherein said protein has L-methionine/branched chain amino acid exporter activity, and
   (D) a protein comprising an amino acid sequence that is at least 90% identical to the amino acid sequence set forth in SEQ ID NO: 2, and wherein said protein has L-methionine/branched chain amino acid exporter activity; or
   wherein said protein having L-methionine/branched chain amino acid exporter activity is encoded by a DNA selected from the group consisting of:
   (a) a yjeH gene,
   (b) a DNA comprising the nucleotide sequence set forth in SEQ ID NO: 1,
   (c) a DNA encoding a protein comprising the amino acid sequence set forth in SEQ ID NO: 2, but which consists of substitution, deletion, insertion and/or addition of 1 to 40 amino acid residues, and wherein said protein has L-methionine/branched chain amino acid exporter activity,
   (d) a DNA encoding a protein comprising an amino acid sequence that is at least 90% identical to the amino acid sequence set forth in SEQ ID NO: 2, and wherein said protein has L-methionine/branched chain amino acid exporter activity, and
   (e) a DNA which is a variant nucleotide sequence of SEQ ID NO: 1 due to the degeneracy of the genetic code.

2. The method of claim 1, wherein said basic L-amino acid is selected from the group consisting of: L-ornithine, L-citrulline, L-arginine, L-histidine, L-lysine, and combinations thereof.

3. The method of claim 1, wherein the DNA encoding the protein having L-methionine/branched chain amino acid exporter activity has been modified increasing the copy number of the DNA in the bacterium, and/or by modifying an expression regulatory region of the DNA, so that the expression of the DNA is enhanced as compared with a non-modified bacterium.

4. The method of claim 1, wherein said bacterium belongs to the genus *Escherichia* or *Pantoea*.

5. The method of claim 4, wherein said bacterium is *Escherichia coli* or *Pantoea ananatis*.

* * * * *

SEQUENCE LISTING

<160> NUMBER OF SEQ ID NOS: 17

<210> SEQ ID NO 1
<211> LENGTH: 1257
<212> TYPE: DNA
<213> ORGANISM: Escherichia coli

<400> SEQUENCE: 1

```
atgagtggac tcaaacaaga actggggctg gcccagggca ttggcctgct atcgacgtca      60
ttattaggca ctggcgtgtt tgccgttcct gcgttagctg cgctggtagc gggcaataac     120
agcctgtggg cgtggcccgt tttgattatc ttagtgttcc cgattgcgat tgtgtttgcg     180
attctgggtc gccactatcc cagcgcaggc ggcgtcgcgc acttcgtcgg tatggcgttt     240
ggttcgcggc ttgagcgagt caccggctgg ctgttttat cggtcattcc cgtgggtttg      300
cctgccgcac tacaaattgc cgccgggttc ggccaggcga tgtttggctg gcatagctgg     360
caactgttgt tggcagaact cggtacgctg gcgctggtgt ggtatatcgg tactcgcggt     420
gccagttcca gtgctaatct acaaaccgtt attgccggac ttatcgtcgc gctgattgtc     480
gctatctggt gggcgggcga tatcaaacct gcgaatatcc cctttccggc acctggtaat     540
atcgaactta ccgggttatt tgctgcgtta tcagtgatgt tctggtgttt tgtcggtctg     600
gaggcatttg cccatctcgc ctcggaattt aaaaatccag agcgtgattt tcctcgtgct     660
ttgatgattg gtctgctgct ggcaggatta gtctactggg gctgtacggt agtcgtctta     720
cacttcgacg cctatggtga aaaaatggcg gcggcagcat cgcttccaaa aattgtagtg     780
cagttgttcg gtgtaggagc gttatggatt gcctgcgtga ttggctatct ggcctgcttt     840
gccagtctca acatttatat acagagcttc gcccgcctgg tctggtcgca ggcgcaacat     900
aatcctgacc actacctggc acgcctctct tctcgccata tcccgaataa tgccctcaat     960
```

```
gcggtgctcg gctgctgtgt ggtgagcact ttggtgattc atgctttaga gatcaatctg    1020
gacgctctta ttatttatgc caatggcatc tttattatga tttatctgtt atgcatgctg    1080
gcaggctgta aattattgca aggacgttat cgactactgg cggtggttgg cgggctgtta    1140
tgcgttctgt tactggcaat ggtcggctgg aaaagtctct atgcgctgat catgctggcg    1200
gggttatggc tgttgctgcc aaaacgaaaa acgccggaaa atggcataac cacataa       1257
```

<210> SEQ ID NO 2
<211> LENGTH: 418
<212> TYPE: PRT
<213> ORGANISM: Escherichia coli

<400> SEQUENCE: 2

```
Met Ser Gly Leu Lys Gln Glu Leu Gly Leu Ala Gln Gly Ile Gly Leu
1               5                   10                  15

Leu Ser Thr Ser Leu Leu Gly Thr Gly Val Phe Ala Val Pro Ala Leu
            20                  25                  30

Ala Ala Leu Val Ala Gly Asn Asn Ser Leu Trp Ala Trp Pro Val Leu
        35                  40                  45

Ile Ile Leu Val Phe Pro Ile Ala Ile Val Phe Ala Ile Leu Gly Arg
    50                  55                  60

His Tyr Pro Ser Ala Gly Gly Val Ala His Phe Val Gly Met Ala Phe
65                  70                  75                  80

Gly Ser Arg Leu Glu Arg Val Thr Gly Trp Leu Phe Leu Ser Val Ile
                85                  90                  95

Pro Val Gly Leu Pro Ala Ala Leu Gln Ile Ala Gly Phe Gly Gln
            100                 105                 110

Ala Met Phe Gly Trp His Ser Trp Gln Leu Leu Leu Ala Glu Leu Gly
        115                 120                 125

Thr Leu Ala Leu Val Trp Tyr Ile Gly Thr Arg Gly Ala Ser Ser Ser
130                 135                 140

Ala Asn Leu Gln Thr Val Ile Ala Gly Leu Ile Val Ala Leu Ile Val
145                 150                 155                 160

Ala Ile Trp Trp Ala Gly Asp Ile Lys Pro Ala Asn Ile Pro Phe Pro
                165                 170                 175

Ala Pro Gly Asn Ile Glu Leu Thr Gly Leu Phe Ala Ala Leu Ser Val
            180                 185                 190

Met Phe Trp Cys Phe Val Gly Leu Glu Ala Phe Ala His Leu Ala Ser
        195                 200                 205

Glu Phe Lys Asn Pro Glu Arg Asp Phe Pro Arg Ala Leu Met Ile Gly
    210                 215                 220

Leu Leu Leu Ala Gly Leu Val Tyr Trp Gly Cys Thr Val Val Leu
225                 230                 235                 240

His Phe Asp Ala Tyr Gly Glu Lys Met Ala Ala Ala Ser Leu Pro
                245                 250                 255

Lys Ile Val Val Gln Leu Phe Gly Val Gly Ala Leu Trp Ile Ala Cys
            260                 265                 270

Val Ile Gly Tyr Leu Ala Cys Phe Ala Ser Leu Asn Ile Tyr Ile Gln
        275                 280                 285

Ser Phe Ala Arg Leu Val Trp Ser Gln Ala Gln His Asn Pro Asp His
    290                 295                 300

Tyr Leu Ala Arg Leu Ser Ser Arg His Ile Pro Asn Asn Ala Leu Asn
305                 310                 315                 320

Ala Val Leu Gly Cys Cys Val Val Ser Thr Leu Val Ile His Ala Leu
```

```
                    325                 330                 335
Glu Ile Asn Leu Asp Ala Leu Ile Ile Tyr Ala Asn Gly Ile Phe Ile
            340                 345                 350

Met Ile Tyr Leu Leu Cys Met Leu Ala Gly Cys Lys Leu Leu Gln Gly
        355                 360                 365

Arg Tyr Arg Leu Leu Ala Val Val Gly Gly Leu Leu Cys Val Leu Leu
    370                 375                 380

Leu Ala Met Val Gly Trp Lys Ser Leu Tyr Ala Leu Ile Met Leu Ala
385                 390                 395                 400

Gly Leu Trp Leu Leu Leu Pro Lys Arg Lys Thr Pro Glu Asn Gly Ile
                405                 410                 415

Thr Thr

<210> SEQ ID NO 3
<211> LENGTH: 20
<212> TYPE: DNA
<213> ORGANISM: Artificial Sequence
<220> FEATURE:
<223> OTHER INFORMATION: Primer P1

<400> SEQUENCE: 3
agaaatgggg atgaggcttc                                              20

<210> SEQ ID NO 4
<211> LENGTH: 21
<212> TYPE: DNA
<213> ORGANISM: Artificial Sequence
<220> FEATURE:
<223> OTHER INFORMATION: Primer P2

<400> SEQUENCE: 4
cctaataatg acgtcgatag c                                            21

<210> SEQ ID NO 5
<211> LENGTH: 5829
<212> TYPE: DNA
<213> ORGANISM: Artificial Sequence
<220> FEATURE:
<223> OTHER INFORMATION: pMW-attL-CmR-attR-Pnlp8 plasmid

<400> SEQUENCE: 5
gacagtaaga cgggtaagcc tgttgatgat accgctgcct tactgggtgc attagccagt     60
ctgaatgacc tgtcacggga taatccgaag tggtcagact ggaaaatcag agggcaggaa    120
ctgctgaaca gcaaaaagtc agatagcacc acatagcaga cccgccataa aacgccctga    180
gaagcccgtg acgggctttt cttgtattat gggtagtttc cttgcatgaa tccataaaag    240
gcgcctgtag tgccatttac ccccattcac tgccagagcc gtgagcgcag cgaactgaat    300
gtcacgaaaa agacagcgac tcaggtgcct gatggtcgga gacaaaagga atattcagcg    360
atttgcccga gcttgcgagg gtgctactta agcctttagg gttttaaggt ctgttttgta    420
gaggagcaaa cagcgtttgc gacatccttt tgtaatactg cggaactgac taaagtagtg    480
agttatacac agggctggga tctattcttt ttatcttttt ttattctttc tttattctat    540
aaattataac cacttgaata taaacaaaaa aaacacacaa aggtctagcg aatttacag    600 agggtctagc agaatttaca agttttccag caaaggtcta gcagaattta cagataccca    660
caactcaaag gaaaaggact agtaattatc attgactagc ccatctcaat ggtatagtg    720 attaaaatca cctagaccaa ttgagatgta tgtctgaatt agttgttttc aaagcaaatg    780
```

```
aactagcgat tagtcgctat gacttaacgg agcatgaaac caagctaatt ttatgctgtg    840
tggcactact caaccccacg attgaaaacc ctacaaggaa agaacggacg gtatcgttca    900
cttataacca atacgctcag atgatgaaca tcagtaggga aaatgcttat ggtgtattag    960
ctaaagcaac cagagagctg atgacgagaa ctgtggaaat caggaatcct ttggttaaag   1020
gctttgagat tttccagtgg acaaactatg ccaagttctc aagcgaaaaa ttagaattag   1080 ttttttaggta agagatattg ccttatcttt tccagttaaa aaaattcata aaatataatc   1140
tggaacatgt taagtctttt gaaaacaaat actctatgag gatttatgag tggttattaa   1200
aagaactaac acaaaagaaa actcacaagg caaatataga gattagcctt gatgaattta   1260
agttcatgtt aatgcttgaa ataactacc atgagtttaa aaggcttaac caatgggttt   1320
tgaaaccaat aagtaaagat ttaaacactt acagcaatat gaaattggtg gttgataagc   1380
gaggccgccc gactgatacg ttgattttcc aagttgaact agatagacaa atggatctcg   1440
taaccgaact tgagaacaac cagataaaaa tgaatggtga caaaatacca acaaccatta   1500
catcagattc ctacctacgt aacggactaa gaaaaacact cacgatgct ttaactgcaa    1560 aaattcagct caccagtttt gaggcaaaat ttttgagtga catgcaaagt aagcatgatc   1620
tcaatggttc gttctcatgg ctcacgcaaa acaacgaac cacactagag aacatactgg    1680
ctaaatacgg aaggatctga ggttcttatg gctcttgtat ctatcagtga agcatcaaga   1740
ctaacaaaca aaagtagaac aactgttcac cgttagatat caaagggaaa actgtccata   1800
tgcacagatg aaaacggtgt aaaaaagata gatacatcag agcttttacg agttttggt    1860 gcatttaaag ctgttcacca tgaacagatc gacaatgtaa cagatgaaca gcatgtaaca   1920
cctaatagaa caggtgaaac cagtaaaaca aagcaactag aacatgaaat tgaacacctg   1980
agacaacttg ttacagctca acagtcacac atagacagcc tgaaacaggc gatgctgctt   2040
atcgaatcaa agctgccgac aacacgggag ccagtgacgc ctcccgtggg gaaaaaatca   2100
tggcaattct ggaagaaata gcgccattcg ccattcaggc tgcgcaactg ttgggaaggg   2160
cgatcggtgc gggcctcttc gctattacgc cagctggcga aaggggatg tgctgcaagg    2220 cgattaagtt gggtaacgcc agggttttcc cagtcacgac gttgtaaaac gacggccagt   2280
gaattcgagc tcggtacccg gggatcccat tacatgggga tcttgaagcc tgcttttta    2340 tactaagttg gcattataaa aaagcattgc ttatcaattt gttgcaacga acaggtcact   2400
atcagtcaaa ataaaatcat tatttgattt cgtcgagtta cgccccgccc tgccactcat   2460
cgcagtactg ttgtaattca ttaagcattc tgccgacatg gaagccatca cagacggcat   2520
gatgaacctg aatcgccagc ggcatcagca ccttgtcgcc ttgcgtataa tatttgccca   2580
tggtgaaaac gggggcgaag aagttgtcca tattggccac gtttaaatca aaactggtga   2640
aactcaccca gggattggct gagacgaaaa acatattctc aataaaccct ttagggaaat   2700
aggccaggtt ttcaccgtaa cacgccacat cttgcgaata tatgtgtaga aactgccgga   2760
aatcgtcgtg gtattcactc cagagcgatg aaaacgtttc agtttgctca tggaaaacgg   2820
tgtaacaagg gtgaacacta tcccatatca ccagctcacc gtctttcatt gccatacgga   2880
attccggatg agcattcatc aggcgggcaa gaatgtgaat aaaggccgga taaaacttgt   2940
gcttattttt ctttacggtc tttaaaaagg ccgtaatatc cagctgaacg gtctggttat   3000
aggtacattg agcaactgac tgaaatgcct caaaatgttc tttacgatgc cattgggata   3060
tatcaacggt ggtatatcca gtgatttttt tctccatttt agcttcctta gctcctgaaa   3120
atctcgataa ctcaaaaaat acgcccggta gtgatcttat ttcattatgg tgaaagttgg   3180
```

```
aacctcttac gtgccgatca acgtctcatt ttcgccaaaa gttggcccag ggcttcccgg   3240
tatcaacagg gacaccagga tttatttatt ctgcgaagtg atcttccgtc acaggtattt   3300
attcggcgca aagtgcgtcg ggtgatgctg ccaacttact gatttagtgt atgatggtgt   3360
ttttgaggtg ctccagtggc ttctgtttct atcagctgtc cctcctgttc agctactgac   3420
ggggtggtgc gtaacggcaa aagcaccgcc ggacatcagc tgcagtctgt tacaggtcac   3480
taataccatc taagtagttg attcatagtg actgcatatg ttgtgtttta cagtattatg   3540
tagtctgttt tttatgcaaa atctaattta atatattgat atttatatca ttttacgttt   3600
ctcgttcagc tttttatac taacttgagc gctaatgacg cagctggacg aaggcgggat    3660
tctcgtctta cccgtagggg aggagcacca gtatttgaaa cgggtgcgtc gtcggggagg   3720
cgaatttatt atcgataccg tggaggccgt gcgctttgtc cctttagtga agggtgagct   3780
ggcttaaaac gtgaggaaat acctggattt ttcctggtta ttttgccgca ggtcagcgta   3840
taatgaagat cttttccagt gttgacaagg gtccttgcac ggttataatg tcactggtta   3900
ttaaccaatt tttcctgggg gataatctag agtcgacctg caggcatgca agcttggcgt   3960
aatcatggtc atagctgttt cctgtgtgaa attgttatcc gctcacaatt ccacacaaca   4020
tacgagccgg aagcataaag tgtaaagcct ggggtgccta atgagtgagc taactcacat   4080
taattgcgtt gcgctcactg cccgctttcc agtcgggaaa cctgtcgtgc cagctgcatt   4140
aatgaatcgg ccaacgcgcg gggagaggcg gtttgcgtat tgggcgcttt ctcaatgctc   4200
acgctgtagg tatctcagtt cggtgtaggt cgttcgctcc aagctgggct gtgtgcacga   4260
accccccgtt cagcccgacc gctgcgcctt atccggtaac tatcgtcttg agtccaaccc   4320
ggtaagacac gacttatcgc cactggcagc agccactggt aacaggatta gcagagcgag   4380
gtatgtaggc ggtgctacag agttcttgaa gtggtggcct aactacggct acactagaag   4440
gacagtattt ggtatctgcg ctctgctgaa gccagttacc ttcggaaaaa gagttggtag   4500
ctcttgatcc ggcaaacaaa ccaccgctgg tagcggtggt ttttttgttt gcaagcagca   4560
gattacgcgc agaaaaaaag gatctcaaga agatcctttg atcttttcta cggggtctga   4620
cgctcagtgg aacgaaaact cacgttaagg gattttggtc atgagattat caaaaaggat   4680
cttcacctag atccttttaa attaaaaatg aagttttaaa tcaatctaaa gtatatatga   4740
gtaaacttgg tctgacagtt accaatgctt aatcagtgag gcacctatct cagcgatctg   4800
tctatttcgt tcatccatag ttgcctgact ccccgtcgtg tagataacta cgatacggga   4860
gggcttacca tctggcccca gtgctgcaat gataccgcga cccacgct caccggctcc      4920 agatttatca gcaataaacc agccagccgg aagggccgag cgcagaagtg gtcctgcaac   4980
tttatccgcc tccatccagt ctattaattg ttgccgggaa gctagagtaa gtagttcgcc   5040
agttaatagt ttgcgcaacg ttgttgccat tgctgcaggc atcgtggtgt cacgctcgtc   5100
gtttggtatg gcttcattca gctccggttc ccaacgatca aggcgagtta catgatcccc   5160
catgttgtgc aaaaaagcgg ttagctcctt cggtcctccg atcgttgtca gaagtaagtt   5220
ggccgcagtg ttatcactca tggttatggc agcactgcat aattctctta ctgtcatgcc   5280
atccgtaaga tgcttttctg tgactggtga gtactcaacc aagtcattct gagaatagtg   5340
tatgcggcga ccgagttgct cttgcccggc gtcaacacgg gataataccg cgccacatag   5400
cagaacttta aaagtgctca tcattggaaa acgttcttcg gggcgaaaac tctcaaggat   5460
cttaccgctg ttgagatcca gttcgatgta acccactcgt gcacccaact gatcttcagc   5520
```

```
atcttttact tccaccagcg tttctgggtg agcaaaaaca ggaaggcaaa atgccgcaaa    5580
aaagggaata agggcgacac ggaaatgttg aatactcata ctcttccttt ttcaatatta    5640
ttgaagcatt tatcagggtt attgtctcat gagcggatac atatttgaat gtatttagaa    5700
aaataaacaa ataggggttc cgcgcacatt tccccgaaaa gtgccacctg acgtctaaga    5760
aaccattatt atcatgacat taacctataa aaataggcgt atcacgaggc cctttcgtct    5820
tcaagaatt                                                            5829
```

```
<210> SEQ ID NO 6
<211> LENGTH: 60
<212> TYPE: DNA
<213> ORGANISM: Artificial Sequence
<220> FEATURE:
<223> OTHER INFORMATION: Primer P3

<400> SEQUENCE: 6
ctgatcagca caaatcgggt gaaaaccct gattcatgaa gcctgctttt ttatactaag    60
```

```
<210> SEQ ID NO 7
<211> LENGTH: 60
<212> TYPE: DNA
<213> ORGANISM: Artificial Sequence
<220> FEATURE:
<223> OTHER INFORMATION: Primer P4

<400> SEQUENCE: 7
ctgggccagc cccagttctt gtttgagtcc actcatttat cccccaggaa aaattggtta    60
```

```
<210> SEQ ID NO 8
<211> LENGTH: 64
<212> TYPE: DNA
<213> ORGANISM: Artificial Sequence
<220> FEATURE:
<223> OTHER INFORMATION: Primer P5

<400> SEQUENCE: 8
taattcaata agtggcgttc gccatgcgag gataaacgct caagttagta taaaaagct    60 gaac                                                                 64
```

```
<210> SEQ ID NO 9
<211> LENGTH: 64
<212> TYPE: DNA
<213> ORGANISM: Artificial Sequence
<220> FEATURE:
<223> OTHER INFORMATION: Primer P6

<400> SEQUENCE: 9
gggtgagggc accaacgcgc agcggaccca atcacttgaa gcctgctttt ttatactaag    60
ttgg                                                                 64
```

```
<210> SEQ ID NO 10
<211> LENGTH: 64
<212> TYPE: DNA
<213> ORGANISM: Artificial Sequence
<220> FEATURE:
<223> OTHER INFORMATION: Primer P7

<400> SEQUENCE: 10
ttagccgcga agctgaaagc cgataagaaa agcggtcgct caagttagta taaaaagct    60 gaac                                                                 64
```

```
<210> SEQ ID NO 11
<211> LENGTH: 64
<212> TYPE: DNA
<213> ORGANISM: Artificial Sequence
<220> FEATURE:
<223> OTHER INFORMATION: Primer P8

<400> SEQUENCE: 11
gacctcatca gtgacttcca taccgccatg taggcctgaa gcctgctttt ttatactaag    60
ttgg                                                                 64

<210> SEQ ID NO 12
<211> LENGTH: 64
<212> TYPE: DNA
<213> ORGANISM: Artificial Sequence
<220> FEATURE:
<223> OTHER INFORMATION: Primer P9

<400> SEQUENCE: 12
tcagttaatt aagcagggtg ttattttatg acgacgcgct caagttagta taaaaaagct    60
gaac                                                                 64

<210> SEQ ID NO 13
<211> LENGTH: 64
<212> TYPE: DNA
<213> ORGANISM: Artificial Sequence
<220> FEATURE:
<223> OTHER INFORMATION: Primer P10

<400> SEQUENCE: 13
gttgatgtcg aattactggc ctttgttttc cagatttgaa gcctgccttt ttatactaag    60
ttgg                                                                 64

<210> SEQ ID NO 14
<211> LENGTH: 63
<212> TYPE: DNA
<213> ORGANISM: Artificial Sequence
<220> FEATURE:
<223> OTHER INFORMATION: Primer P11

<400> SEQUENCE: 14
tcttgcaaaa acagcctgcg ttttcatcag taatagcgct caagttagta taaaaaagcg    60
aac                                                                  63

<210> SEQ ID NO 15
<211> LENGTH: 66
<212> TYPE: DNA
<213> ORGANISM: Artificial Sequence
<220> FEATURE:
<223> OTHER INFORMATION: Primer P12

<400> SEQUENCE: 15
agcggcggta atgttctcaa acatgacgag gtttccttag ctgtttcctt ctagacggcc    60
aatgct                                                               66

<210> SEQ ID NO 16
<211> LENGTH: 22
<212> TYPE: DNA
<213> ORGANISM: Artificial Sequence
<220> FEATURE:
<223> OTHER INFORMATION: Primer P13

<400> SEQUENCE: 16
```

```
cgtttaccag ttctaatagc ac                                              22

<210> SEQ ID NO 17
<211> LENGTH: 21
<212> TYPE: DNA
<213> ORGANISM: Artificial Sequence
<220> FEATURE:
<223> OTHER INFORMATION: Primer P14

<400> SEQUENCE: 17
tttatagaca ccaatcccga g                                               21
```